United States Patent
Suzuki

(10) Patent No.: US 8,672,952 B2
(45) Date of Patent: Mar. 18, 2014

(54) CLOSE-WOUND COIL AND MEDICAL TREATMENT TOOL USING THIS COIL

(75) Inventor: Takayuki Suzuki, Yokohama (JP)

(73) Assignee: Olympus Corporation, Tokyo (JP)

( * ) Notice: Subject to any disclaimer, the term of this patent is extended or adjusted under 35 U.S.C. 154(b) by 625 days.

(21) Appl. No.: 12/420,596

(22) Filed: Apr. 8, 2009

(65) Prior Publication Data

US 2009/0198103 A1 Aug. 6, 2009

Related U.S. Application Data

(63) Continuation of application No. 10/790,261, filed on Mar. 1, 2004, now abandoned.

(30) Foreign Application Priority Data

Mar. 3, 2003 (JP) ................................. 2003-056215

(51) Int. Cl.
*A61B 17/10* (2006.01)

(52) U.S. Cl.
USPC ........................................................ 606/142

(58) Field of Classification Search
USPC ......... 606/205, 206, 167, 170, 171, 174, 143, 606/159, 51, 52, 142; 600/562, 564, 141; 604/22

See application file for complete search history.

(56) References Cited

U.S. PATENT DOCUMENTS

| | | | |
|---|---|---|---|
| 4,308,740 A | 1/1982 | Brauer | |
| 5,437,282 A | 8/1995 | Koger et al. | |
| 5,439,478 A * | 8/1995 | Palmer | 606/205 |
| 5,478,350 A * | 12/1995 | Kratsch et al. | 606/205 |
| 6,443,909 B1 | 9/2002 | Ouchi | |
| 6,540,670 B1 | 4/2003 | Hirata et al. | |
| 6,824,548 B2 | 11/2004 | Smith et al. | |
| 2002/0045909 A1* | 4/2002 | Kimura et al. | 606/151 |
| 2003/0028206 A1 | 2/2003 | Shiber | |

FOREIGN PATENT DOCUMENTS

| | | |
|---|---|---|
| FR | 1504917 | 12/1967 |
| GB | 13017 | 0/1910 |
| JP | 55-109501 | 8/1980 |
| JP | 56-112221 | 9/1981 |
| JP | 8-131550 | 5/1996 |
| JP | 2001-321386 | 11/2001 |
| JP | 2002-210019 | 7/2002 |
| JP | 2002-272751 | 9/2002 |

OTHER PUBLICATIONS

Japanese Official Action dated Nov. 29, 2011 from related application JP 2009-230798.

* cited by examiner

*Primary Examiner* — S. Thomas Hughes
*Assistant Examiner* — Tin Nguyen
(74) *Attorney, Agent, or Firm* — Scully, Scott, Murphy & Pressure, PC

(57) ABSTRACT

A medical treatment tool is provided having: a force transmission member having a distal end and a proximal end; an end effector which is provided on the distal end of the force transmission member in a non-rotatable manner with respect to the force transmission member; a control wire which is inserted into the force transmission member; and a rotatable coupling which is provided between the end effector and the control wire, and is coupled rotatably to the end effector with respect to the control wire.

5 Claims, 20 Drawing Sheets

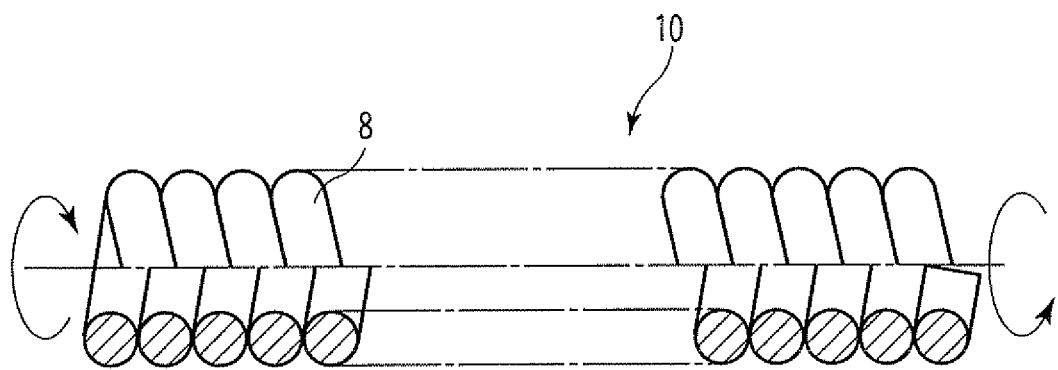
FIG. 2
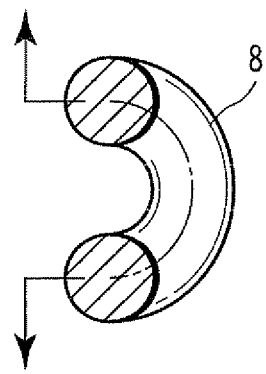
FIG. 3A        FIG. 3B
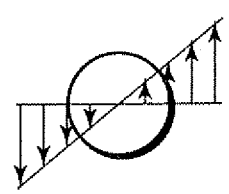      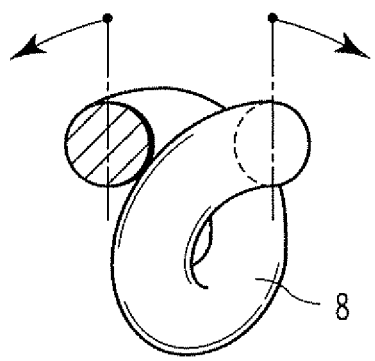
FIG. 4A        FIG. 4B

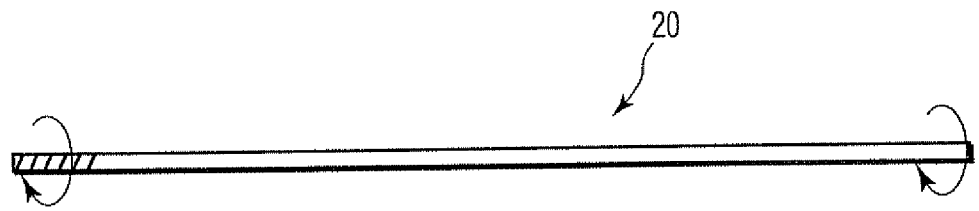
F I G. 12
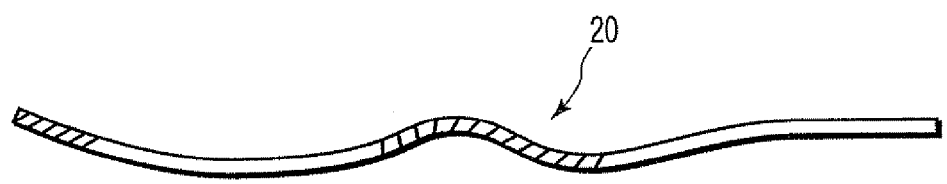
F I G. 13A
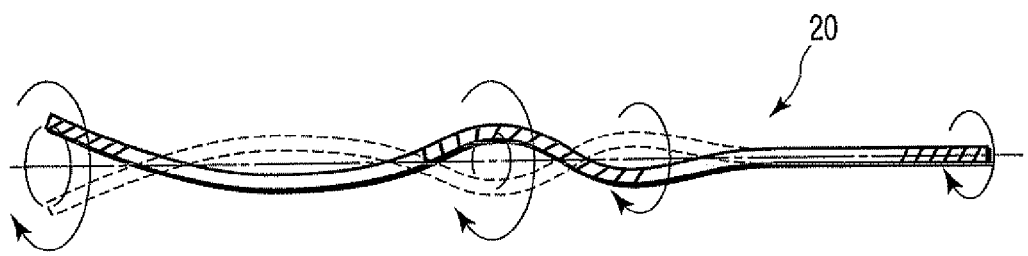
F I G. 13B
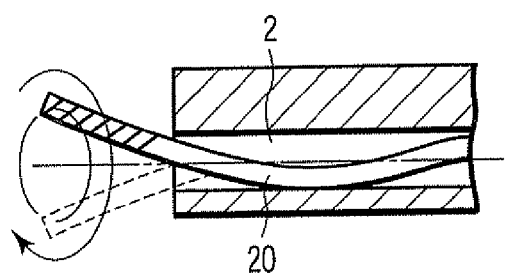
F I G. 13C

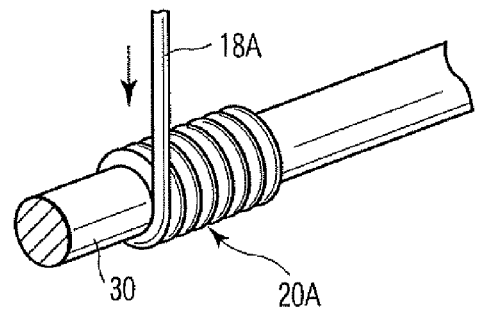
F I G. 16
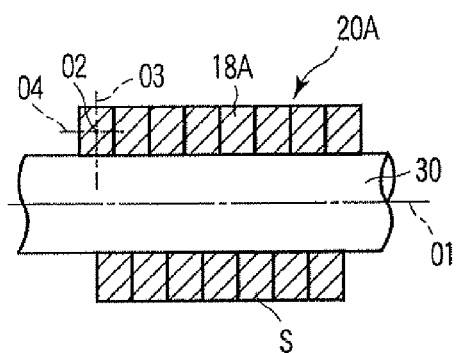
F I G. 17A
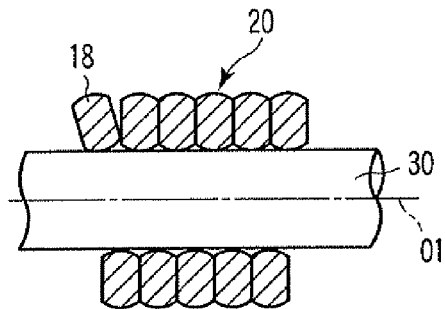
F I G. 17B
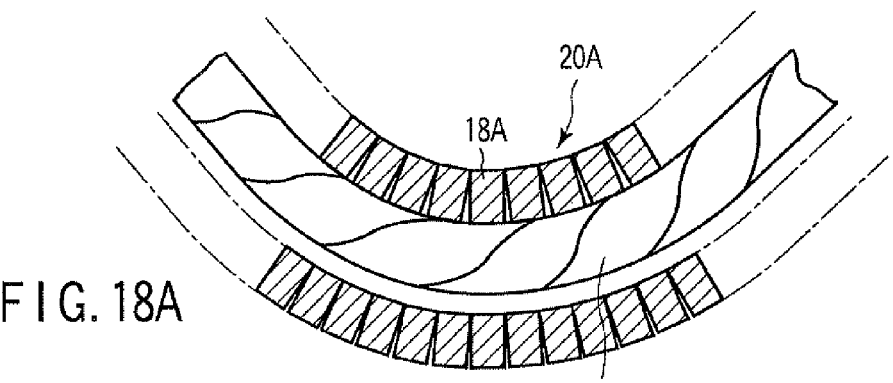
F I G. 18A
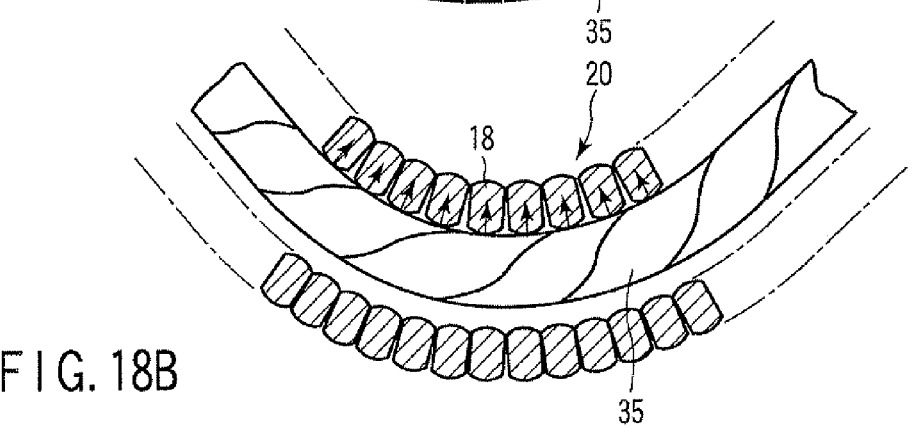
F I G. 18B

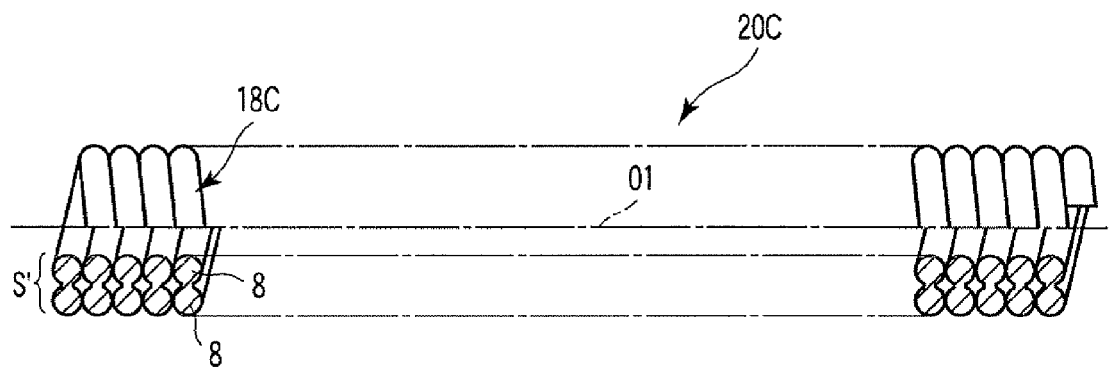
F I G. 26
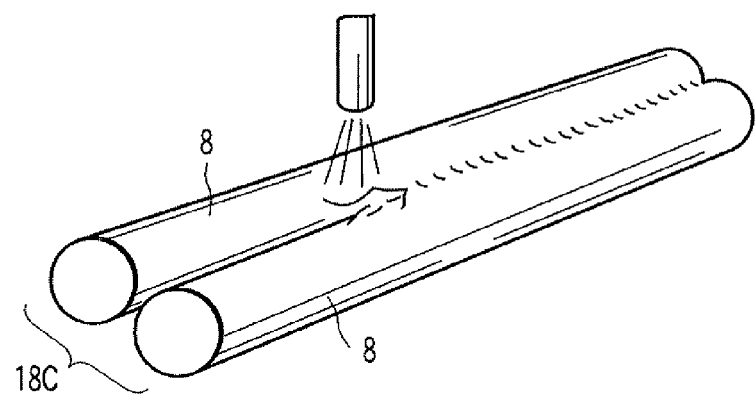
F I G. 27

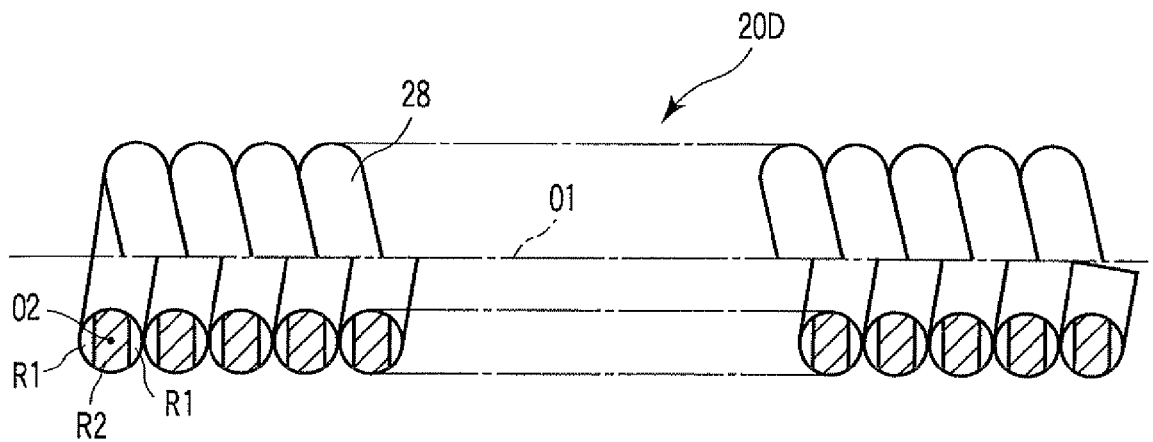
FIG. 28
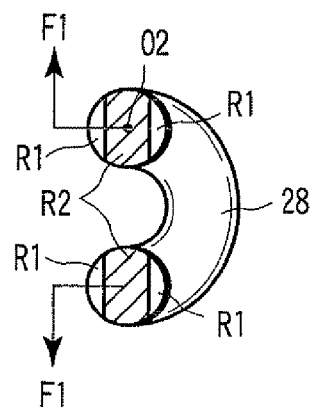   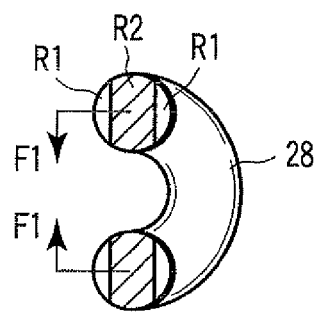
FIG. 29A          FIG. 29B
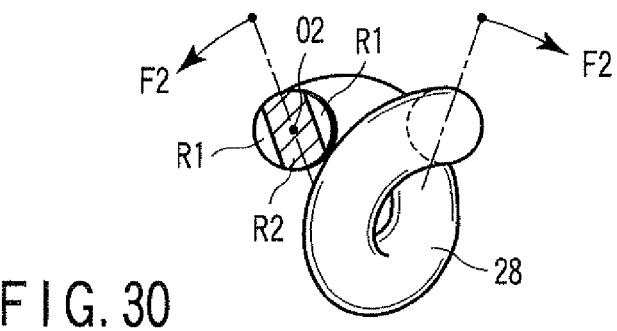
FIG. 30

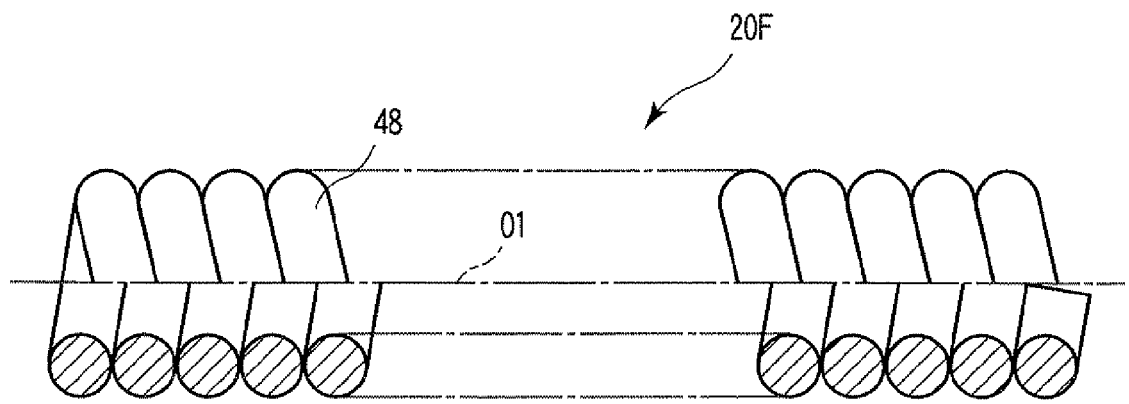
F I G. 34
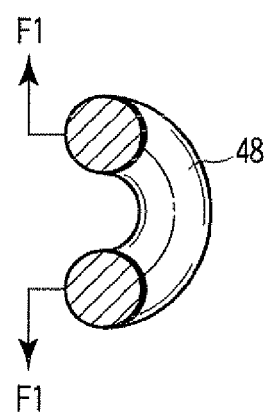
F I G. 35A
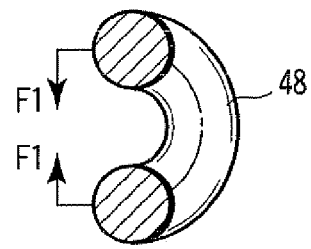
F I G. 35B
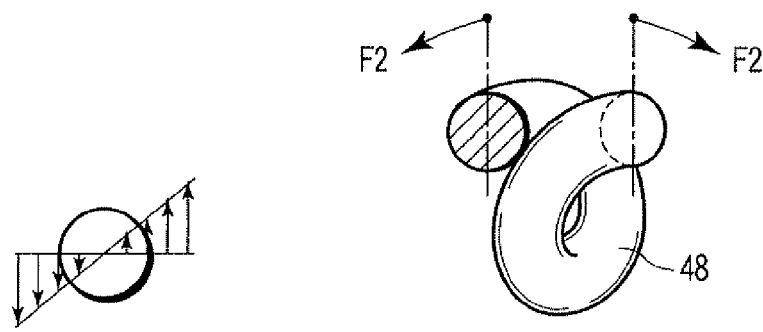
F I G. 36A          F I G. 36B

CLOSE-WOUND COIL AND MEDICAL TREATMENT TOOL USING THIS COIL

CROSS-REFERENCE TO RELATED APPLICATIONS

This application is a continuation application of U.S. patent application Ser. No. 10/790,261 filed Mar. 1, 2004, now abandoned, which is based upon and claims the benefit of priority from prior Japanese Patent Application No. 2003-056215, filed Mar. 3, 2003, the entire contents of each of which are incorporated herein by reference.

BACKGROUND OF THE INVENTION

1. Field of the Invention

The present invention relates to a close-wound coil formed by winding a wire spirally and closely over a predetermined length, and a medical treatment tool using the close-wound coil.

2. Description of the Related Art

Generally, a medical treatment tool inserted into a human body through an endoscope channel comprises a treatment section provided at a distal end, a control section provided at a proximal end, and a transmission member to transmit the operating force from the control section to the treatment section.

The transmission member is inserted into an elongated channel extended in an endoscope which is inserted into a winding tubular abdominal cavity, and required not only to withstand bending and compressing but to transmit the operating force from the control section to the treatment section.

Thus, as described in Jpn. Pat. Appln. KOKAI Publication No. 56-112221, a close-wound coil formed by winding a wire with a circular section spirally and closely over a predetermined length, is widely used as a force transmission member.

FIG. 42 schematically illustrates an example of a conventional medical treatment tool having such a close-wound coil as a force transmission member. As illustrated in the drawing, a medical treatment tool 100 comprises a treatment section 102 provided at a distal end, an operation section 106 provided at a proximal end, and a close-wound coil 104 which connects the operation section 106 and treatment section 102. An endoscope 200 to lead the medical treatment tool 100 into a human body is provided with an insertion part 202 to be inserted into a tubular cavity in the body, and a control section 206 at a proximal end. A channel 208 to insert the medical treatment tool 100 is formed in the insertion part 202. At the distal end of the insertion part 202, a bending section 204 that is bent by a control knob (not shown) provided in the control section 206 is provided.

There is one serious problem in a conventional close-wound coil. That is, as shown in FIG. 42, when the endoscope 200 is led into a winding tubular abdominal cavity and the insertion section 202 of the endoscope 200 is bent complexly, the close-wound coil 104 of the medical treatment tool 100 inserted into the channel 208 of the insertion section 202 is also bent complexly over a long distance. Thus, even if the operation section 106 is rotated and the rotation force is transmitted to the treatment section 102 through the close-wound coil 104 in order to change the position of the treatment tool 102, for example, the treatment tool 102 may not rotate as intended due to various factors concerning the close-wound coil 104. Particularly, in the state that the bending section 204 is curved at a large angle with a small radius of curvature, it is very difficult to transmit the rotation force proportionally to the treatment section 102 at the end of the bending section 204.

FIG. 43 shows schematically the rotation transmission performance of a conventional close-wound coil in the bent state shown in FIG. 42. As indicated by a solid line, in a conventional close-wound coil, even if the operation section 106 is rotated in the bent state shown in FIG. 42, a delay or skip (unevenness) occurs in the rotation of the close-wound coil 104, and the treatment section 102 cannot follow faithfully the rotation of the close-wound coil 104. Namely, as indicated by a dashed line in FIG. 43, it is ideal that the rotation angle (input angle) of the operation section 106 appears directly as a rotation angle (output angle) of the treatment section 102 (input angle=output angle), but actually as indicated by a solid line in FIG. 43, a delay occurs between the input angle and output angle due to a rotation delay or rotation skip (input angle−delay angle=output angle), and the rotation output is not stabilized and fine adjustment to a desired rotation angle is difficult.

BRIEF SUMMARY OF THE INVENTION

The present invention has been made in order to solve the above problems. Accordingly, it is an object of the present invention to provide a close-wound coil having a good rotation transmission performance, and a medical treatment tool using the close-wound coil.

According to an aspect of the present invention, there is provided a close-wound coil comprising a first predetermined axis, and a wire which is wound spirally and closely over a predetermined length around the first axis, and has a center axis extending in the length direction thereof. The wire has a section vertical to the center axis, a second axis passing across the center axis within the section and vertical to the first axis, and a third axis passing across the center axis within the section and vertical to the second axis. The wire has substantially the same flexural rigidity as that of a reference wire having a perfect circle section with a diameter of the longer one of section along the second axis and section along third axis and the torsional rigidity of the wire is lower than the torsional rigidity of the reference wire.

According to another aspect of the present invention, there is provided a close-wound coil comprising a first predetermined axis, and a wire which is wound spirally and closely over a predetermined length around the first axis, and has a center axis extending in the length direction thereof. The wire has a section vertical to the center axis, a second axis passing across the center axis within the section and vertical to the first axis, and a third axis passing across the center axis within the section and vertical to the second axis. The section is formed to have the second moment of area concerning the second axis smaller than the second moment of area concerning the third axis.

According to another aspect of the present invention, there is provided a close-wound coil comprising a first predetermined axis, and a wire which is wound spirally and closely over a predetermined length around the first axis, and has a center axis extending in the length direction thereof. The wire has a section vertical to the center axis, a second axis passing across the center axis within the section and vertical to the first axis, and a third axis passing across the center axis within the section and vertical to the second axis. The section is formed to have the dimension along the second axis larger than the dimension along the third axis.

According to another aspect of the present invention, there is provided a medical treatment tool comprising a close-wound coil having a distal end and a proximal end. The close-wound coil comprising a first axis extending between the distal end and proximal end, and a wire which is wound spirally and closely over a predetermined length around the first axis, and has a center axis extending in the length direction. The wire has a section vertical to the center axis, a second axis passing across the center axis within the section and vertical to the first axis, and a third axis passing across the center axis within the section and vertical to the second axis. The medical treatment tool further comprising a rotation control section which is provided in the proximal end of the close-wound coil, for rotating the close-wound coil around the first axis, and a treatment section which is located closer to the distal end than the close-wound coil, and receives the rotation control force from the rotation control section through the close-wound coil. The wire has substantially the same flexural rigidity as that of a reference wire having a perfect circle section with a diameter of predetermined dimension, and the torsional rigidity of the wire is lower than the torsional rigidity of the reference wire.

According to another aspect of the present invention, there is provided a medical treatment tool used in combination with a medical endoscope, the medical treatment tool comprising a mantle tube, and a close-wound coil inserted into the mantle tube, the close-wound coil having a first axis extending between the distal end and proximal end, and a wire which is wound spirally and closely over a predetermined length around the first axis, and has a center axis extending in the length direction thereof. The wire has a section vertical to the center axis, a second axis passing across the center axis within the section and vertical to the first axis, and a third axis passing across the center axis within the section and vertical to the second axis. The medical treatment tool further comprises a control section for rotating the close-wound coil with respect to the mantle tube. The wire has substantially the same flexural rigidity as that of a reference wire having a perfect circle section with a predetermined dimension. The torsional rigidity of the wire is lower than the torsional rigidity of the reference wire.

According to another aspect of the present invention, there is provided a treatment tool for an endoscope used in combination with a medical endoscope having a slender channel. The treatment tool for an endoscope comprises a close-wound coil which can be inserted into the channel. The close-wound coil comprises a first axis extending between the distal end and proximal end, and a wire which is wound spirally and closely over a predetermined length around the first axis, and has a center axis extending in the length direction thereof. The wire has a section vertical to the center axis, a second axis passing across the center axis within the section and vertical to the first axis, and a third axis passing across the center axis within the section and vertical to the second axis. The treatment tool further comprises a rotary part which is provided in the close-wound coil, and rotates the close-wound coil with respect to the channel. The wire has substantially the same flexural rigidity as that of a reference wire having a perfect circle section with a predetermined dimension, and the torsional rigidity of the wire is lower than the torsional rigidity of the reference wire.

As explained above, according to the present invention, there is provided a close-wound coil having a good rotation transmission performance, and a medical treatment tool using the close-wound coil.

Advantages of the invention will be set forth in the description which follows, and in part will be obvious from the description, or may be learned by practice of the invention.

Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a half sectional view of a close-wound coil comprising a wire with a circular section;

FIG. 3A is a conceptual view showing the bent state of a part of a wire forming a bending beam when the close-wound coil of FIG. 2 is twisted in the direction opposite to the winding direction;

FIG. 3B is a conceptual view showing the bent state of a part of a wire forming a bending beam when the close-wound coil of FIG. 2 is twisted in the winding direction;

FIG. 4A is a conceptual view showing the twisted state of a wire when the close-wound coil of FIG. 2 is bent;

FIG. 4B illustrates a distribution of stress in a wire when a torsional torque acts on a wire as shown in FIG. 4A;

FIG. 12 is a side view of a close-wound coil with high straightness;

FIG. 13A is a side view of a curled close-wound coil;

FIG. 13B is a schematic view showing generation of a swing when a curved close-wound coil is rotated;

FIG. 13C is a sectional view showing a bad influence by a swing during insertion into an endoscope channel;

FIG. 16 is a perspective view showing a part of a manufacturing method of the close-wound coil of FIG. 15;

FIG. 17A is a side sectional view of FIG. 16;

FIG. 17B is a side sectional view corresponding to FIG. 17A when manufacturing the close-wound coil of FIG. 5;

FIG. 18A is a sectional view showing a first example of the use form of the close-wound coil of FIG. 15;

FIG. 18B is a sectional view showing a first example of the use form of the close-wound coil of FIG. 5;

FIG. 26 is a half section view of a modified example of the close-wound coil of FIG. 23;

FIG. 27 is a perspective view showing the state of welding wires;

FIG. 28 is a half section view of a close-wound coil according to a fifth embodiment of the present invention;

FIG. 29A is a conceptual view showing the bent state of a part of a wire forming a bending beam when the close-wound coil of FIG. 28 is twisted in the direction opposite to the winding direction;

FIG. 29B is a conceptual illustration showing the bent state of a part of a wire forming a bending beam when the close-wound coil of FIG. 28 is twisted in the winding direction;

FIG. 30 is a conceptual view showing the twisted state of a wire when the close-wound coil of FIG. 28 is bent;

FIG. 34 is a half section view of a close-wound coil according to a seventh embodiment of the present invention;

FIG. 35A is a conceptual view showing the bent state of a part of a wire forming a bending beam when the close-wound coil of FIG. 34 is twisted in the direction opposite to the winding direction;

FIG. 35B is a conceptual view showing the bent state of a part of a wire forming a bending beam when the close-wound coil of FIG. 34 is twisted in the winding direction;

FIG. 36A is a conceptual view showing the twisted state of a wire when the close-wound coil of FIG. 34 is bent;

FIG. 36B illustrates a distribution of stress in a wire when a torsional torque acts on a wire as shown in FIG. 36A;

DETAILED DESCRIPTION OF THE INVENTION

Before describing embodiments of the present invention, explanation will be given on the basic concept of the invention.

Figure 43:
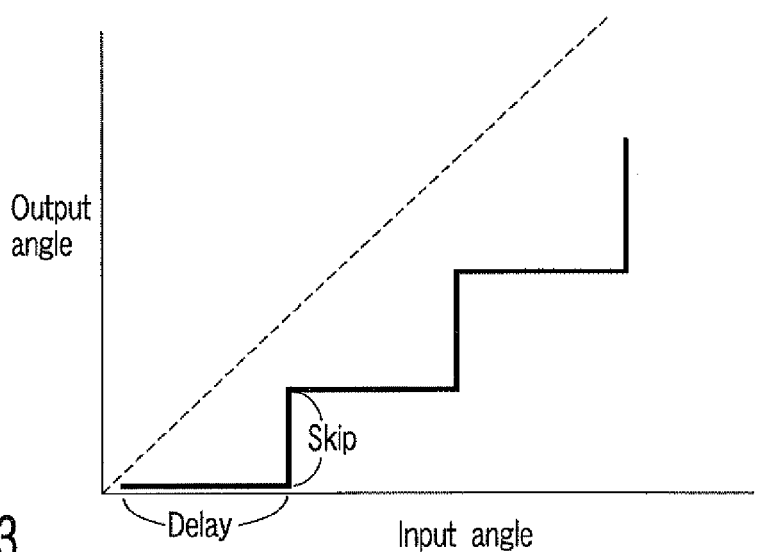
FIG. 43 is a graph showing the rotation transmission performance of the close-wound coil formed by a wire with a circular section under predetermined conditions.

In a conventional close-wound coil, there are two primary causes of generating a delay between an input angle and an output angle (refer to FIG. 43).

One is accumulation of stress by torsional deformation of a close-wound coil when a close-wound coil is not a rigid body. Namely, when rotation force is inputted and a close-wound coil causes torsional deformation, a part of the rotation force is accumulated as an internal stress in the close-wound coil. Thus, the rotation angle outputted at the other end of the close-wound coil becomes not identical to the rotation angle inputted from one end. Therefore, when the torsional rigidity of the close-wound coil is large, accumulation of stress in the close-wound coil is small, a delay or skip is difficult to occur during rotation, and the rotation transmission performance is high. Contrarily, when the torsional rigidity of the close-wound coil is small, accumulation of stress in the close-wound coil is large, a delay or skip is easy to occur during rotation, and the rotation transmission performance is low.

Figure 1:
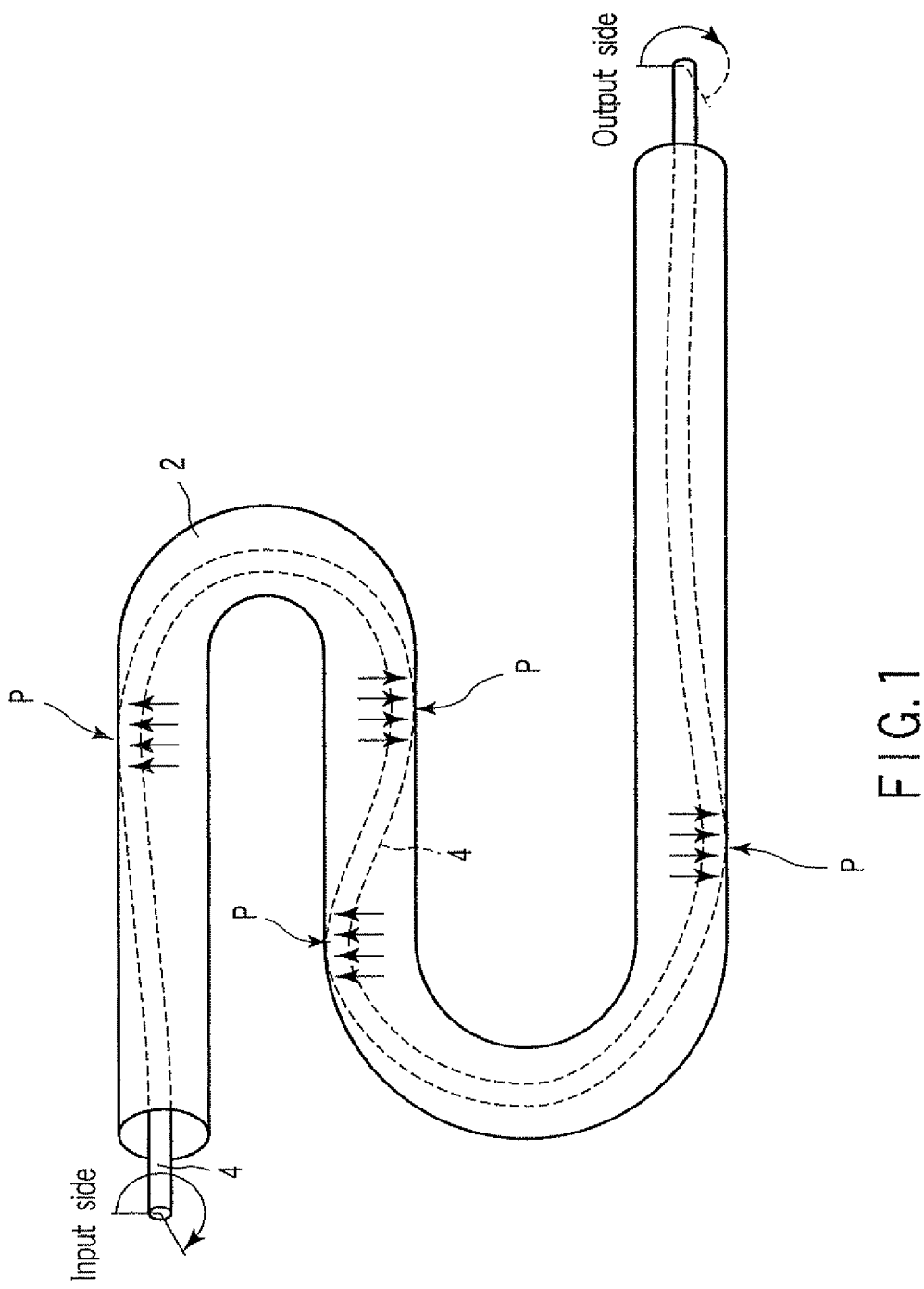
FIG. 1 is a schematic view showing a close-wound coil inserted into a complexly winding endoscope channel.

The second cause of generating a delay between an input angle and an output angle is frictional resistance generated between an endoscope channel and a close-wound coil. Namely, as shown in FIG. 1, in the state that close-wound coil 4 is inserted into an endoscope channel 2, the close-wound coil 4 is pressed to contact to the inside surface of the channel 2, thereby generating frictional resistance. In this case, when the flexural rigidity of the close-wound coil 4 is small, the contact pressure of the close-wound coil 4 to the channel 2 at a contact point P is small, and the frictional resistance is decreased. However, when the flexural rigidity of the close-wound coil 4 is large, the contact pressure of the close-wound coil 4 to the channel 2 at the contact point P is large, and the frictional resistance is increased.

Considering the above two causes, it is necessary to decrease accumulation of stress by the torsional deformation of a close-wound coil and decrease the frictional resistance generated between the close-wound coil and endoscope channel, for improving the rotation transmission performance of a close-wound coil. Namely, the rotation transmission performance of a close-wound coil can be increased by increasing the torsional rigidity of a close-wound coil and decreasing the flexural rigidity of a close-wound coil.

The torsional rigidity and flexural rigidity of a close-wound coil are originally considered to correspond to the torsional rigidity and flexural rigidity of a wire forming a close-wound coil. Namely, as shown in FIG. 2, considering the close-wound coil 10 formed by winding a wire 8 with a circular section spirally and closely over a predetermined length, the torsion of the close-wound coil 10 corresponds to the flex of the wire 8 as shown in FIGS. 3A and 3B. Concretely, when the close-wound coil 10 is twisted in the winding direction, the position of the wire 8 forming a curved beam is bent inward as shown in FIG. 3B. Contrarily, when the close-wound coil 10 is twisted in the direction opposite to the winding direction, the position of the wire 8 forming a curved beam is bent outward as shown in FIG. 3A. Therefore, the torsional rigidity of the close-wound coil 10 corresponds to the flexural rigidity of the wire 8 forming the close-wound coil 10.

On the other hand, the flex of the close-wound coil 10 corresponds to the torsion of the wire 8 as shown in FIGS. 4A and 4B. Because, when the close-wound coil 10 is bent, the wire 8 is deformed and the adjacent windings are separated each other, to receive the force in the twisting direction. Therefore, the flexural rigidity of the close-wound coil 10 corresponds to the torsional rigidity of the wire 8 forming the close-wound coil 10. FIG. 4B shows the stress distribution in the wire 8 when the torsional torque acts on the wire 8 as shown in FIG. 4A.

The above discussion is summarized that it is necessary to increase the torsional rigidity of the close-wound coil 10 and decrease the flexural rigidity of the close-wound coil 10 for improving the rotation transmission performance of the close-wound coil 10. For this purpose, it is necessary to increase the flexural rigidity of the wire 8 forming the close-wound coil 10 and decrease the torsional rigidity of the wire 8.

However, the conventional close-wound coil 10 does not easily satisfy the above conditions. Because, the wire 8 of the conventional close-wound coil 10 has a circular section, and if the outside diameter of the wire 8 is increased to improve the torsional rigidity of the close-wound coil 10, the flexural rigidity of the close-wound coil 10 is also increased. Therefore, when the wire 8 has a circular section, it is difficult to improve the rotation performance of the close-wound coil 10 merely by changing the outside diameter.

The applicant of the present application considered all the above points, and as a result, found that the correlation between the second moment of area in the wire has a great concern to the above conditions under certain conditions. Further, the applicant of the present application also found that the above conditions are easily satisfied under certain conditions, even if the wire has a circular section.

Hereinafter, explanation will be given on the concrete embodiments based on the above findings (the concept of the present invention).

Figure 5:
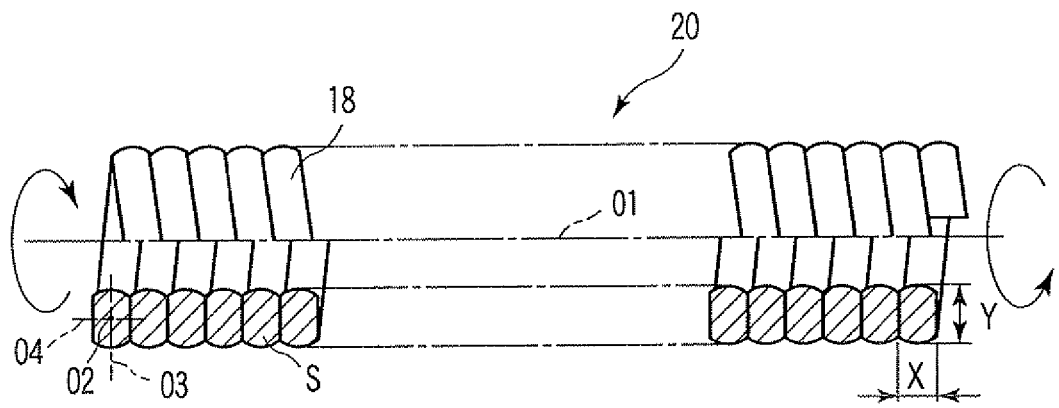
FIG. 5 is a half section view of the close-wound coil according to a first embodiment of the present invention.

FIG. 5 to FIG. 7 show a first embodiment of the present invention.

As shown in FIG. 5, a close-wound coil 20 is formed by winding a wire 18 with a non-circular section spirally and closely over a predetermined length around a predetermined first axis O1. The wire 18 is formed so that in a section S vertical to a center axis O2 extending in the lengthwise direction of the wire, the second moment of area $I_1$ concerning a second axis O3 passing across a center axis O2 and vertical to the first axis O1 is smaller than the second moment of area $I_2$ concerning a third axis O4 passing across the center axis O2 of the section S and vertical to the second axis O3. Concretely, the section S of the wire 18 is substantially rectangular where the dimension Y along the second axis O3 is larger than the dimension X along the third axis O4 (the vertical-to-horizontal ratio of the section S is larger than 1, and has an arc with a large curvature at both ends along the second axis O3). In other words, the close-wound coil 20 is formed in arrangement that the sections S of the adjacent windings of the wire 18 are closely contacted in the shorter radius direction (the state shown in FIG. 5). The above section shape of the wire 18 is formed at a low cost by rolling a wire with a circular section in the direction along the third axis O4, for example.

Further, in this embodiment, the dimension of the section S of the wire 18 is set, so that the torsional rigidity becomes equivalent to (substantially identical to) that of a wire having a perfect circle section with a diameter d (hereinafter, this is referred to as a first reference wire). Concretely, considering the wire 18 by approximating to a rectangle with a vertical dimension Y and a horizontal dimension X, the relation of X, Y to d is set to:

$$d = (32\xi_1 YX^3/\pi)^{1/4} \quad (1)$$

Where, $\xi_1$ is a constant determined by Y/X.

The equation (1) is led as follows.

Namely, the torsion angle φ when a torsional moment T is applied to a rod with the length L is:

(i) When the section is circular, $$\phi_R = 32TL/\pi d^4 G$$

(G is a horizontal elastic coefficient (a constant determined by material)), (ii) When the section is rectangular, $$\phi_R = TL/\xi_1 YX^3 G \ (X > X)$$

The equivalent torsional rigidity means that the torsion angle (deformation amount) when the same torsional moment is applied is the same, and $$\phi_R = \phi_L$$

Therefore, $$32TL/\pi d^4 G = TL/\xi_1 YX^3 G$$

As a result, $$d = (32\xi_1 YX^3/\pi)^{1/4}$$

Further, as the wire 18 in this embodiment, a corrosion-proof material resistant to flexural deformation, tensile load and compressive load is preferable. For example, there are stainless steel wire for a spring (SUS304-WPB, SUS316-WPA, SUS301, SUS302-WPB, SUS631J1-WPC) defined by Japan Industrial Standard), nickel-titanium alloy (with super-elasticity), piano wire, oil tempered wire and tungsten wire.

Figure 6A:
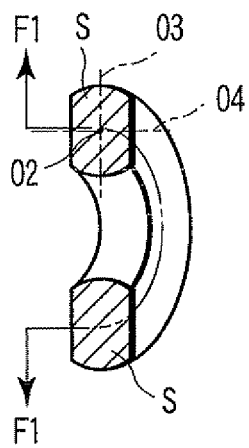
FIG. 6A is a conceptual view showing the bent state of a part of a wire forming a bending beam when the close-wound coil of FIG. 5 is twisted in the direction opposite to the winding direction.
Figure 6B:
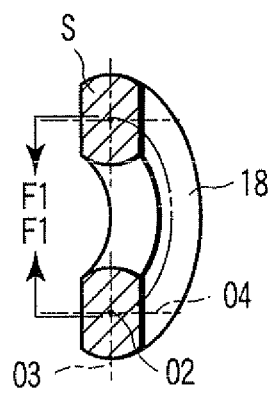
FIG. 6B is a conceptual view showing the bent state of a part of a wire forming a bending beam when the close-wound coil of FIG. 5 is twisted in the winding direction.

As described above, in the close-wound coil 20 of this embodiment, the wire 18 is formed so that the second moment of area $I_2$ concerning the third axis O4 is larger than the second moment of area $I_1$ concerning the second axis O3. Thus, it is possible to increase the flexural rigidity of the wire 18 forming a bending beam (refer to FIGS. 6A and 6B showing the state that the bending force F1 is acted on the wire 18) in the direction along the second axis O3. Therefore, the torsional rigidity of the close-wound coil 20 can be increased compared with that of a conventional close-wound coil formed by a circular wire. As a result, the rotation transmission performance (rotation following performance) can be increased.

Figure 7A:
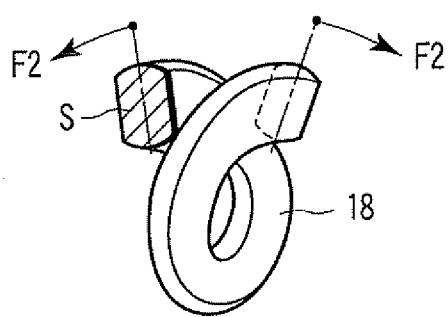
FIG. 7A is a conceptual view showing the twisted state of a wire when the close-wound coil of FIG. 5 is bent.
Figure 7B:
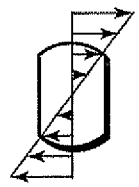
FIG. 7B illustrates a distribution of stress in a wire when a torsional torque acts on a wire as shown in FIG. 7A.

Particularly, in the close-wound coil 20 of this embodiment, in addition to the relation between the second moment of area $I_1$ and $I_2$, the dimension of the section S of the wire 18 is set so that the torsional rigidity of the wire 18 is equivalent to the torsional rigidity of the first reference wire. (FIGS. 7A and 7B show the state that a twisting force F2 is acted on the wire 18). Therefore, the flexural rigidity of the close-wound coil 20 is equivalent to the corresponding flexural rigidity of a close-wound coil formed by the first reference wire having the above-mentioned circular section with a diameter d (hereinafter, referred to as a first reference close-wound coil).

Further, when the torsional rigidity of the wire 18 is set equivalent to the torsional rigidity of the first reference wire, the flexural rigidity of the wire 18 is inevitably larger than that of the first reference wire. For example, when the torsional rigidity is the same in a rectangular-section wire (wire 18) with a vertical dimension Y and horizontal dimension X (Y=1.5X) and a circular-section wire with a diameter d (the first reference wire), the second moment of area $I_L$ and $I_R$ are calculated, (i) The second moment of area $I_L$ of the rectangular-section wire (the wire 18) with the vertical dimension Y and horizontal dimension X (Y=1.5X) is:

$$I_L = Y^3 X/12$$
$$= (1.5X)^3 X/12$$
$$= 0.2812 X^4$$

(ii) The second moment of area $I_R$ of the circular-section wire (the first reference wire) with a diameter d is:

$$I_R = \pi r^4/4 \quad (2)$$
$$= (\pi/4)(d/2)^4$$

Assign the equation (1) to the equation (2) based on the condition that the torsional rigidity is equivalent.

$$I_R = (\pi/64)(32 \xi_1 Y X^3/\pi)$$

Further, when Y=1.5X and $\xi_1$=0.1958:

$$I_R = (\pi/64)(32 \times 0.1958 \times 1.5 X^4/\pi)$$
$$= 0.1468 X^4$$

Therefore, $I_L/I_R$=1.91, and the flexural rigidity of the wire 18 with a rectangular section ($EI_L$ (E is elasticity) is double the flexural rigidity of the first reference wire (with a circular section) ($EI_R$). (Therefore, the torsional rigidity of the close-wound 20 is double the first reference close-wound coil.)

Namely, in the close-wound coil 20 of this embodiment, the torsional rigidity is larger than that of the first reference close-wound coil, and the flexural rigidity is equivalent to that of the first reference close-wound coil. Therefore, the rotation transmission performance (rotation following performance) is increased to higher than the first reference close-wound coil.

Further, with the close-wound coil 20 of this embodiment, the following various functions and effects as explained hereinafter with reference to FIG. 8A to FIG. 14B can be obtained by accomplishing the above explained characteristics and form.

Figure 8A:
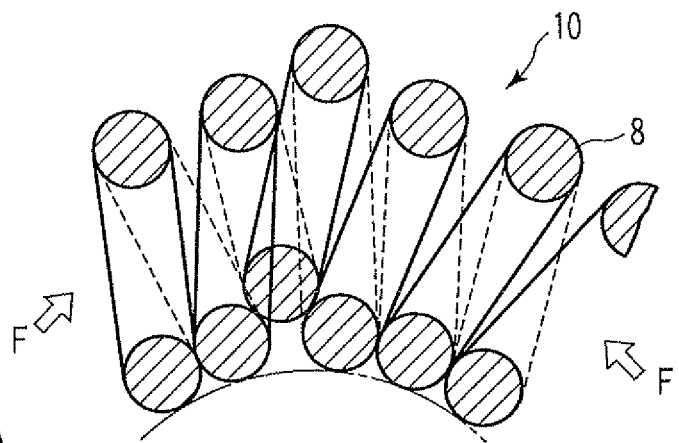
FIG. 8A is a sectional view showing defective deformation of a close-wound coil formed by a conventional wire with a circular section.
Figure 8B:
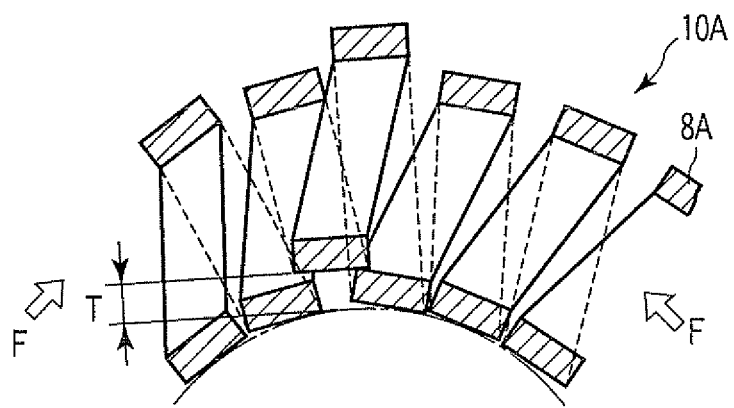
FIG. 8B is a sectional view showing defective deformation of a close-wound coil formed by a conventional wire with a rectangular section.

Namely, if a wire has a circular section as in a conventionally, the wires 8 of the coil 10 contact at a point as shown in FIG. 8A, and when a strong compressive force F is acted on both ends while the coil 10 is being curved, the wires 8 are displaced and easily deformed permanently. Further, as shown in FIG. 8B, even if the section shape of the wire 8A is not circular but rectangular, when the dimension of the section in the horizontal direction (the length direction of the coil 10A) is longer than the dimension in the vertical direction, the wires 8A overlap in the radial direction, the coil length is contracted, and more serious deformation is caused. Thus, there arise a problem of causing permanent deformation more easily.

Figure 8C:
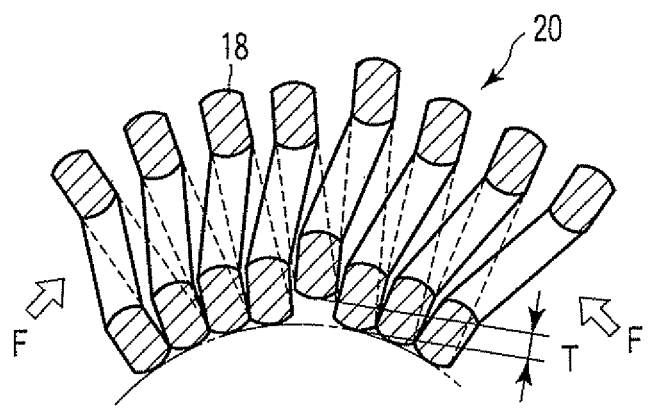
FIG. 8C is a sectional view showing the deformed state of the close-wound coil of FIG. 5.

Contrarily, in the close-wound coil 20 of this embodiment, since the vertical-to-horizontal ratio of the section S of the wire 18 is larger than 1, and the section of the wire 18 is substantially rectangular, the wires 18 contact in a face and hardly to displace (FIG. 8C). Further, since there is an allowance in the vertical length of the contact area of the wires 18, the wires 18 are hardly to overlap in the radial direction even if displayed by the same amount T as the conventional (refer to FIGS. 8B and 8C). Therefore, permanent deformation is difficult to occur, and the compression resistance is improved.

Figure 42:
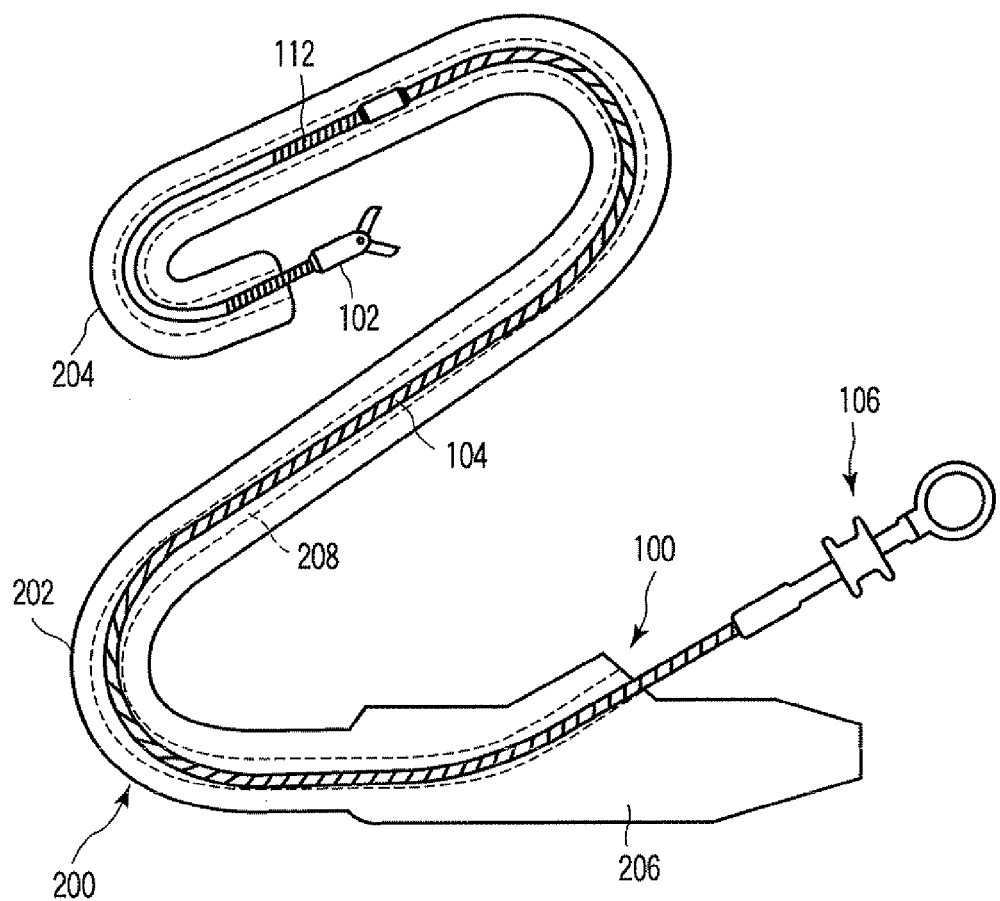
FIG. 42 is a schematic illustration showing the state that a conventional treatment tool is inserted into an endoscope channel.

Further, in a conventional form, as shown in FIG. 42, an another highly flexible close-wound coil 112 is connected to the distal end of the close-wound coil 104, so that the treatment tool 100 can pass smoothly through the bending section at the distal end of the endoscope 200. However, if the highly flexible coil 112 is interposed between the treatment section 102 and close-wound coil 104, the torsional rigidity of the whole close-wound coil is lowered compared with the form with the close-wound coil 104 only, and as a result the rotation transmission performance is further decreased.

On the other hand, the close-wound coil 20 of this embodiment has a flexural rigidity lower than the conventional one as described above, and can pass smoothly through the bending section of an endoscope. Therefore, it is unnecessary to connect another coil with a high torsional rigidity (high flexibility), and the rotation performance is not decreased.

In the close-wound coil 20 of this embodiment, the torsional rigidity of the wire 18 is equivalent to the torsional rigidity of the reference wire, but no problem even if it is lower than the torsional rigidity of the reference wire. This can further increase the rotation transmission performance of the close-wound coil 20.

Figure 9:
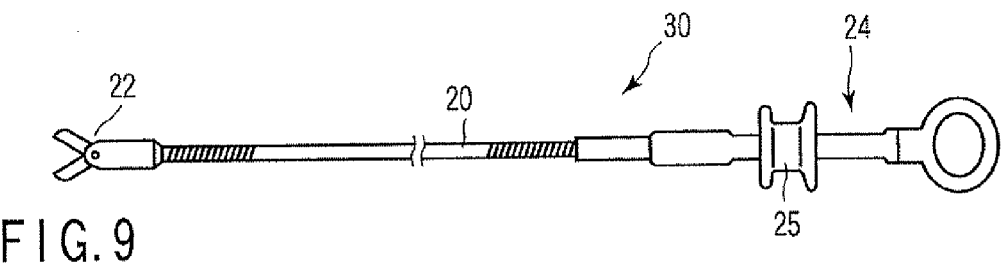
FIG. 9 is a side view showing an example of a medical treatment tool to which the close-wound coil of FIG. 5 is applied.

Further, as shown in FIG. 9, when the close-wound coil 20 of this embodiment is applied to a medical treatment tool 30, a treatment section (end effector) 22 is fixed to the distal end of the close-wound coil 20, and a control section 24 is fixed to the proximal end of the close-wound coil 20. Further, a control wire is inserted into the inside hole of the close-wound coil 20, a movable element of the end effector 22 is connected to the distal end of the control wire, and a handle 25 provided movably in the control section 24 is connected to the proximal end of the control wire. Therefore, in this configuration, when the handle 25 is moved forward and rearward with respect to the control section, the control wire is moved forward and rearward with respect to the close-wound coil 20, and the end effector 22 is operated. When the whole control section 24 is rotated, the torsional torque is transmitted to the close-wound coil 20, and the end effector 22 at the distal end of the close-wound coil 20 is rotated. In this time, the rotation transmissivity is very good because of the above-mentioned reason. As the end effector 22, it is permitted to use biopsy forceps, grasping forceps, a snare to flow a high-frequency current, and basket forceps.

Figure 10A:
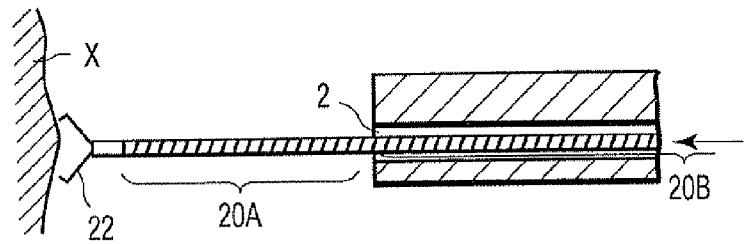
FIG. 10A is a schematic view showing the state that the medical treatment tool provided with the close-wound coil according to the first embodiment of the present invention is pressed to the tissue of a human body through an endoscope.
Figure 10B:
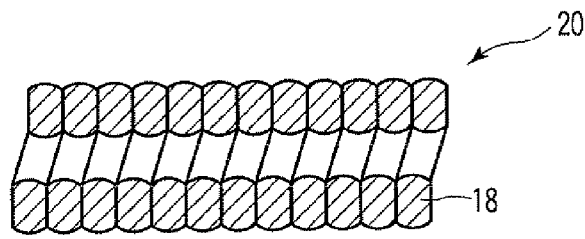
FIG. 10B is a sectional view showing the straight state of the close-wound coil in the situation of FIG. 8A.
Figure 11A:
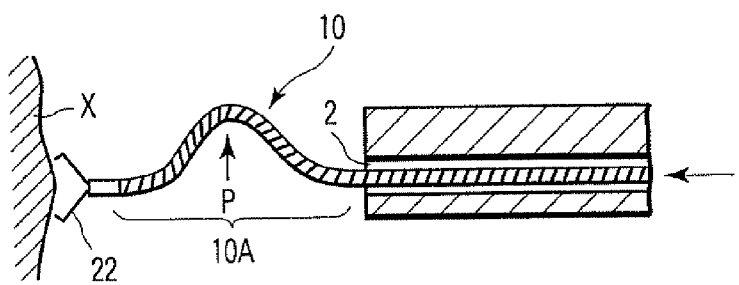
FIG. 11A is a schematic view showing the state that a medical treatment tool provided with a close-wound coil formed by a conventional wire with a circular section is pressed to the tissue of a human body through an endoscope.
Figure 11B:
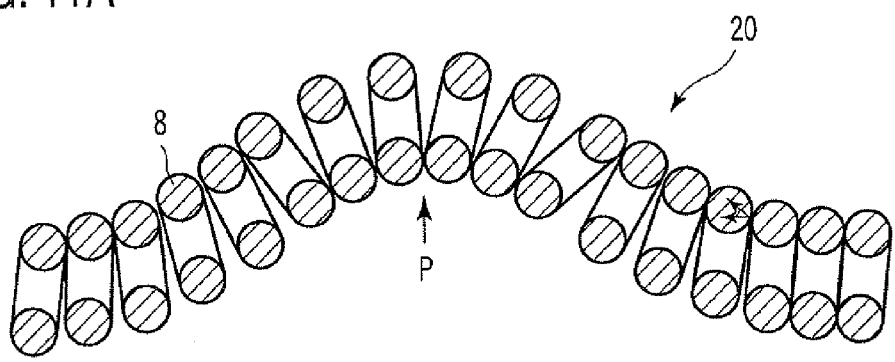
FIG. 11B is a sectional view showing the bent state of the close-wound coil in the situation of FIG. 11A.
Figure 14A:
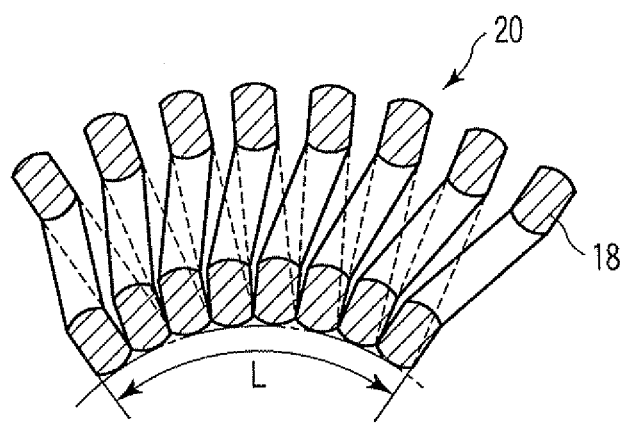
FIG. 14A is a sectional view showing the number of turns per a unit length of the close-wound coil of FIG. 5.
Figure 14B:
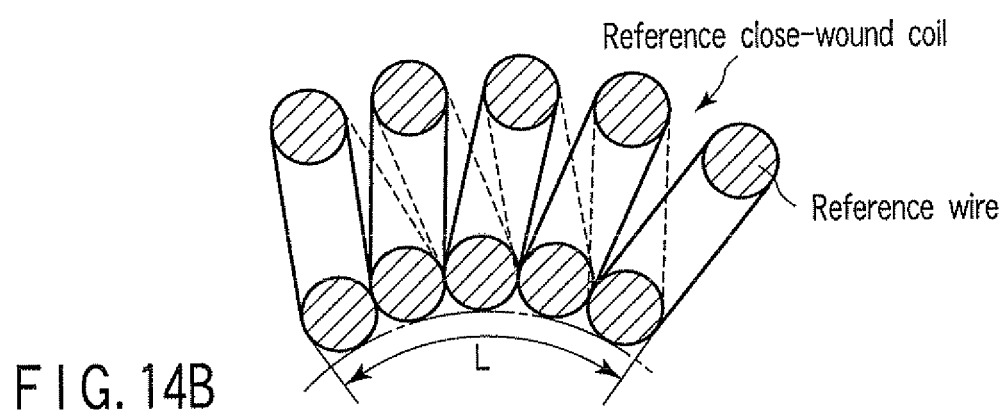
FIG. 14B is a sectional view showing the number of turns per a unit length of a reference close-wound coil.

Assuming that the end effector 22 is exposed to the channel 2 of an endoscope and the end effector 22 is pressed to a tissue X to treat the tissue X in an abdominal cavity, when the close-wound coil 20 of this embodiment is applied to a medical treatment tool, there is no restriction by the channel 2 in the radial direction in the distal end part 20A, unlike the proximal end part 20B located inside of the channel 2. In such a case, when the end effector 22 is pressed to the tissue X, the conventional close-wound coil 10 formed by the circular-section wire 8 is buckled at the middle portion P in the distal end side part 10A of the close-wound coil 10 exposed between the tissue X and endoscope (a compressive force is acted, and the coil is bent sideways). Because, the wires 8 are contacted at a point in the conventional circular-section wire 8, and the compressive force is easy to escape sideways (refer to FIG. 11B). On the other hand, in the close-wound coil 20 of the above-mentioned embodiment, the wires 18 are contacted in a face, and the compressive force is difficult to escape sideways (FIG. 10B), and a buckle is hardly to occur (FIG. 10A).

When making a close-wound coil 20 (not limited to the close-wound coil of this embodiment, but applicable to general ordinary close-wound coils), it is to be noted that the completed close-wound coil 20 has a high straightness as shown in FIG. 12. A high straightness means the property that when one end of the close-wound coil 20 is rotated as shown in FIG. 12, a swing does not occur in each part of the close-wound coil 20, and the coil is rotated while being kept straight.

Contrarily, if there is a curve in a part of the close-wound coil 20 (refer to FIG. 13A), a swing occurs in each part of the coil (refer to FIG. 13B). Particularly, if there is a curve at other end (the distal end at which the end effector 22 is provided) of the close-wound coil 20, the influence becomes serious. Because, when a swing occurs, a friction resistance is generated by the curve between the outside surface of the coil and the inside of the channel 2, though an endoscope is not bent (refer to FIG. 13C).

In the above-mentioned first embodiment, the torsional rigidity of the wire 18 is equivalent to the torsional rigidity of the first reference wire. However, it is permitted to set the dimension of the section S of the wire 18, so that the flexural rigidity of the wire 18 becomes equivalent to (substantially equal to) that of a wire having a section shape of a perfect circle with a diameter d' (hereinafter, referred to as a second reference wire)(namely, the second moment of area $I_2$ concerning the third axis O4 becomes equivalent to that of the second reference wire). In this case, also, the rotation transmission performance (rotation following performance) of the close-wound coil 20 is increased to higher than the rotation transmission performance of a close-wound coil formed by the second reference wire (hereinafter, referred to as a second reference close-wound coil).

Concretely, considering the wire 18 to be approximate to a rectangular shape with a vertical dimension Y and a horizontal dimension X, set the relation of Y, X to d' (Y>X, Y=1.5X) to:

$$d' = (16Y^3 X/3\pi)^{1/4} \quad (3)$$

The equation (3) is led out as follows.

Namely, the second moment of area $I_L$ and $I_R$ of the wire 18 and second reference wire are:

$$I_L = Y^3 X/12$$

$$I_R = \pi r^2/4 = \pi d'^4/64$$

Based on the condition that the flexural rigidity is the same, assuming that:

$$I_L = I_R$$

and, $$Y^3 X/12 = \pi d'^4/64$$

According to this equation, $$d' = (16Y^3 X/3\pi)^{1/4}$$

Further, when the flexural rigidity of the wire 18 is set to equivalent to the flexural rigidity of the second reference wire, the torsional rigidity of the wire 18 becomes inevitably smaller than that of the second reference wire.

Namely, the torsion angle π when a torsional moment T is applied to a rod with the length L is:

(i) When the section is circular $$\phi_R = 32TL/\pi d'^4 G \quad (4)$$

Assign the equation (3) to the equation (4) based on the condition that the torsional rigidity is equivalent.

$$\phi R = (32TL/\pi G)(3\pi/16Y^3 X)$$

$$= 6TL/1.5^3 X^4 G$$

$$= 1.78(TL/X^4 G)$$

(ii) When the section is rectangular $$\phi L = TL/\xi_1 YX^3 G$$

$$= (1/(0.1958 \times 1.5))(TL/X^4 G)$$

$$= 3.40(TL/X^4 G)$$

Therefore, $\phi_R/\phi_L = 0.52$, and the torsional rigidity of the wire 18 becomes about ½ of the torsional rigidity of the second reference wire.

Namely, when the dimension of the section S of the wire 18 is set so that the flexural rigidity of the wire 18 is equivalent to (substantially equal to) that of the second reference wire, the torsional rigidity of the wire 18 becomes smaller than that of the second reference wire. Therefore, the flexural rigidity of the close-wound coil 20 becomes smaller than that of the close-wound coil formed by the second reference wire, and the torsional rigidity of the close-wound coil 20 becomes equivalent to that of the close-wound coil formed by the second reference wire. As a result, the rotation transmission performance (rotation following performance) of the close-wound coil 20 is increased to higher than that of the close-wound coil formed by the second reference wire.

From the viewpoint of setting the dimension of the section S of the wire 18 so that the flexural rigidity of the wire 18 becomes equivalent to (substantially equal to) that of a predetermined circular wire, it is possible to assume a third reference wire whose section shape is a perfect circle with a diameter equal to the longer one (the dimension Y in the first embodiment) of a dimension along the second axis O3 and a dimension along the third axis O4 of the cross section S, and set the flexural rigidity of the wire to substantially the same as the flexural rigidity of the third reference wire. In this case, also, the rotation transmission performance (rotation following performance) of the close-wound coil 20 is increased to higher than that of the close-wound coil (the third reference close-wound coil). Namely, by making the flexural rigidity of the wire 18 equivalent to that of the third reference wire and the cross section of the wire 18 smaller than that of the third reference wire, the torsional rigidity of the wire 18 becomes lower than that of the third reference wire, the flexural rigidity of the close-wound coil 20 becomes lower than that of the third reference close-wound coil, and the short diameter (the dimension X in this embodiment) of the section S of the wire 18 becomes smaller than the diameter of the circular section of the third reference wire. Thus, the number of windings per the unit length L (refer to FIG. 14A) of the close-wound coil 20 becomes more than the number of windings (refer to FIG. 14B) per the unit length L of the third reference close-wound coil, and the deformation amount of the wire 18 with respect to excessive curving (the load applied to one winding of the wire 18) becomes small (i.e., the coil becomes hard to break). Therefore, the resistance caused by the bending of the close-wound coil 20 with respect to a predetermined curving becomes small. Thus, as a whole unit, the rotation performance of the close-wound coil 20 is increased to higher than that of the third reference close-wound coil, and the same function and effect as those of the above-mentioned embodiment can be obtained.

FIG. 15 to FIG. 17B shows a second embodiment of the present invention. In the various embodiments explained hereinafter, the parts common to those of the first embodiment are denoted by the same reference numerals, and the detailed explanation will be omitted.

Figure 15:
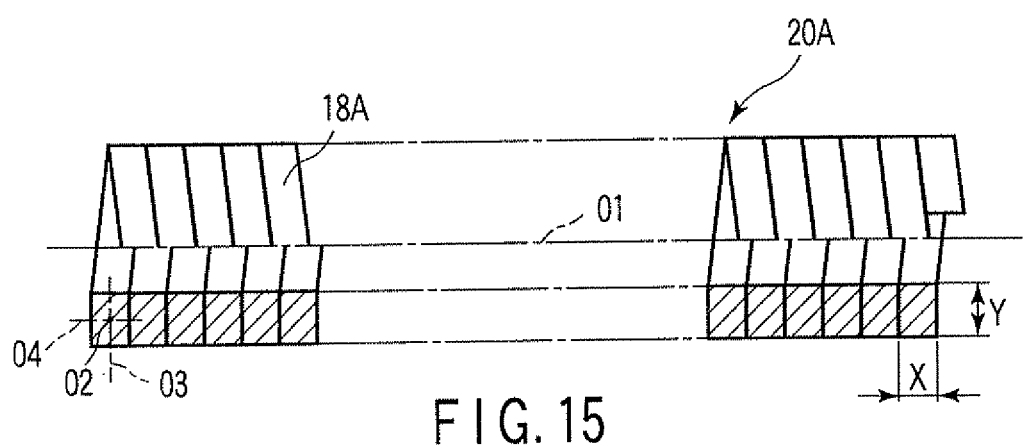
FIG. 15 is a half section view of a close-wound coil according to a second embodiment of the present invention.

As shown in FIG. 15, the section shape of the wire 18A of the close-wound coil 20A of this embodiment is rectangular whose dimension Y along the second axis O3 is larger than the dimension X along the third axis O4. The other characteristics and shapes are the same as the first embodiment.

As described above, in the close-wound coil 20A of this embodiment, the section shape of the wire 18A is rectangular, and advantageous effects can be obtained in the manufacturing process. Namely, when manufacturing the close-wound coil 20A of this embodiment, the wire 18A is wound around a core metal 30 so that the second axis O3 becomes orthogonal to the first axis O1 as shown in FIG. 16. In this process, the wire 18A abuts on the core metal 30 with a flat surface as shown in FIG. 17A, and the wire 18A is hard to fall down with respect to the core metal 30, enabling stable production.

FIG. 17B shows the state that the wire 18 falls down with respect to the core metal 30 in the process of manufacturing the close-wound coil 20 of the first embodiment. With the section shape abutting on the core metal 30 with the arc portion as the wire 18 of the first embodiment, it is considerable that the wire 18 falls down with respect to the core metal 30 in the manufacturing process. On the other hand, with the section shape that the wire 18A abuts on the core metal 30 with a plane (flat portion), the wire 18A becomes hard to fall down with respect to the core metal 30, improving the yield of manufacturing.

The flat portion of the section of the wire of the close-wound coil 20A of this embodiment functions more advantageously than the arc portion of the section of the wire of the close-wound coil 20 of the first embodiment. For example, consider the case where a control wire 35 is inserted into the close-wound coils 20, 20A, as shown in FIGS. 18A and 18B. In the close-wound coil 20 of the first embodiment, as shown in FIG. 18B, the control wire 35 comes into contact with the close-wound coil 20 at points by the inside uneven surface (arc portion) of the close-wound coil 20. Thus if the close-wound coil 20 is curved with a large curvature, the control wire 35 is pressed strongly to these point-contacting portions, a load is collected to these portions (indicated by an arrow in the drawing), and the sliding resistance of the control wire 35 is increased. Therefore, not only the movement of the control wire 35 but the movement of the end effector operated by the control wire 35 becomes heavy. Contrarily, in the close-wound coil 20A of the second embodiment, as shown in FIG. 18A, the control wire 35 comes into contact with the close-wound coil 20A in the inside flat surface of the close-wound coil 20A, the sliding resistance of the control wire 35 is low, and not only the movement of the control wire 35 but the movement of the end effector operated by the control wire 35 becomes light.

Figure 19A:
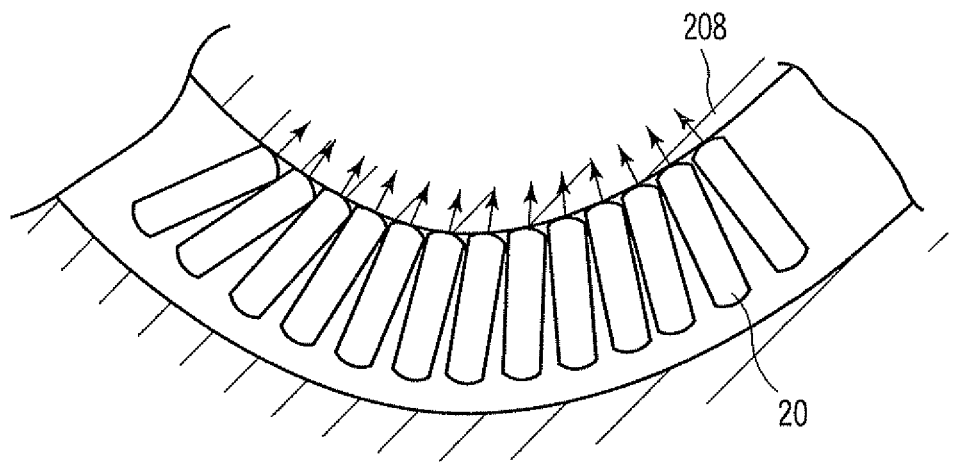
FIG. 19A is a sectional view showing a second example of the use form of the close-wound coil of FIG. 15.
Figure 19B:
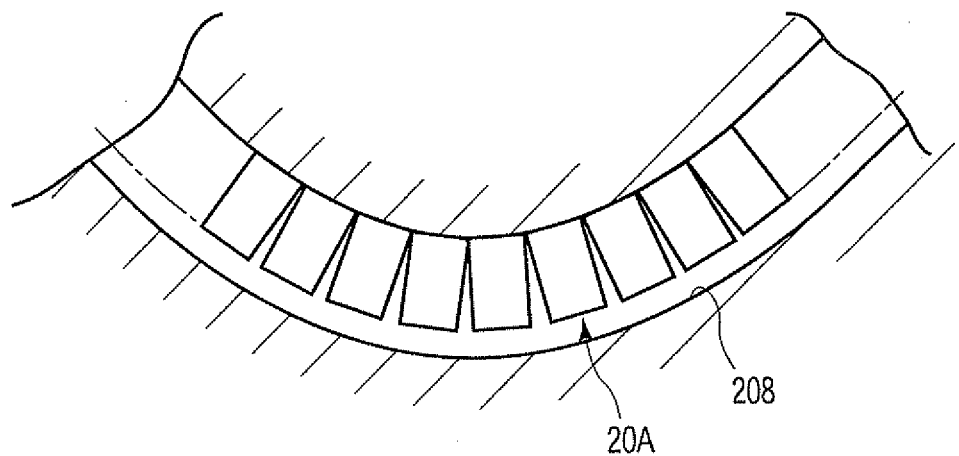
FIG. 19B is a sectional view showing a second example of the use form of the close-wound coil of FIG. 5.
Figure 20:
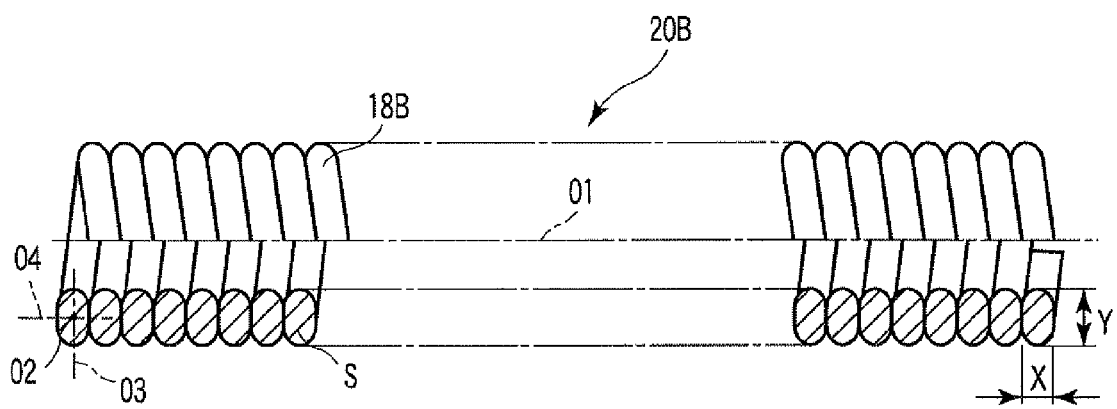
FIG. 20 is a half section view of a close-wound coil according to a third embodiment of the present invention.
Figure 21:
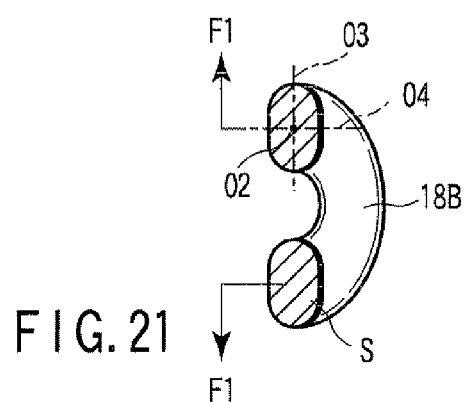
FIG. 21 is a conceptual view showing the bent state of a part of a wire forming a bending beam when the close-wound coil of FIG. 20 is twisted in the direction opposite to the winding direction.
Figures 22A, 22B:
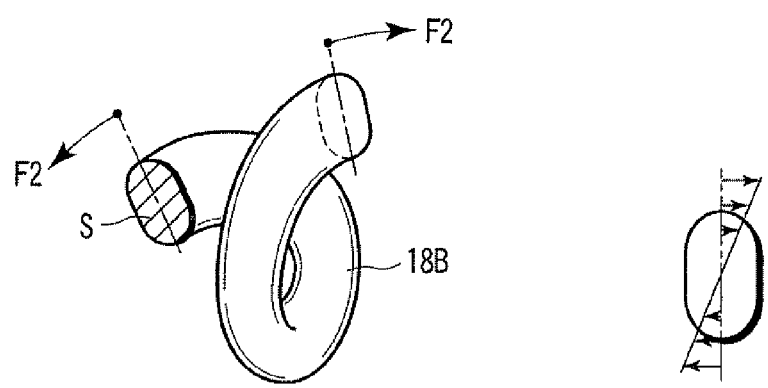
FIG. 22A is a conceptual illustration showing the twisted state of a wire when the close-wound coil of FIG. 20 is bent.
FIG. 22B illustrates a distribution of stress in a wire when a torsional torque acts on a wire as shown in FIG. 22A.

Next, consider the case where the close-wound coils 20 and 20A are inserted into the channel 208 of an endoscope as shown in FIGS. 19A and 19B. In the close-wound coil 20 of the first embodiment, as shown in FIG. 19A, the close-wound coil 20 comes into contact with the inside of the endoscope channel 208 at points by the outside uneven surface (arc portion) of the close-wound coil 20. Thus, if the endoscope channel 208 is curved with a large curvature, a load is concentrated at these portions (indicated by an arrow in the drawing), and the sliding resistance of the close-wound coil 20 is increased. Therefore, the forward/rearward movement or rotation of the close-wound coil 20 (or the treatment section provided at the distal end of the close-wound coil 20) becomes heavy. Contrarily, in the close-wound coil 20A of the second embodiment, the inside of the endoscope channel 208 comes into contact with the close-wound coil 20A in a face by the flat outside surface of the close-wound coil 20A as shown in FIG. 19B, and the sliding resistance of the close-wound coil 20A is low. Therefore, the forward/rearward movement or rotation of the close-wound coil 20A (or the treatment section provided at the distal end of the close-wound coil 20) becomes light.

FIG. 20 to FIG. 22B show a third embodiment of the present invention.

As shown in these drawings, the close-wound coil 20B of this embodiment is formed by a wire 18B with the elliptical section. The other characteristics and shapes are the same as the first embodiment. Therefore, the same functions and effects as those of the first embodiment can be obtained.

Figure 23:
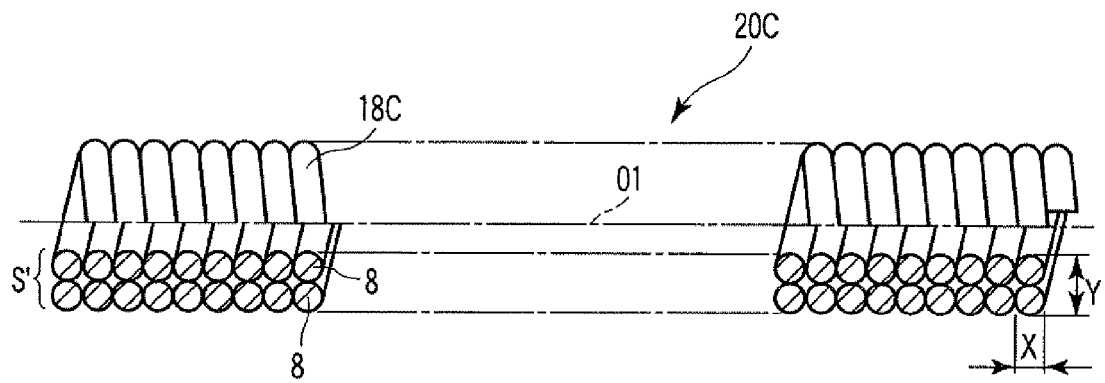
FIG. 23 is a half section view of a close-wound coil according to a fourth embodiment of the present invention.
Figure 24:
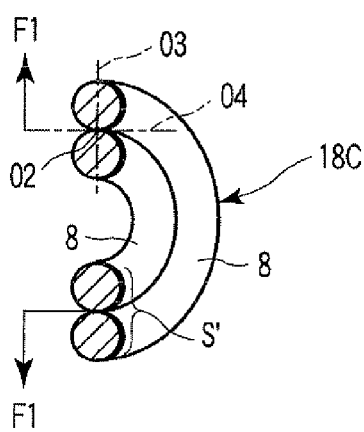
FIG. 24 is a conceptual view showing the bent state of a part of a wire forming a bending beam when the close-wound coil of FIG. 23 is twisted in the direction opposite to the winding direction.
Figure 25:
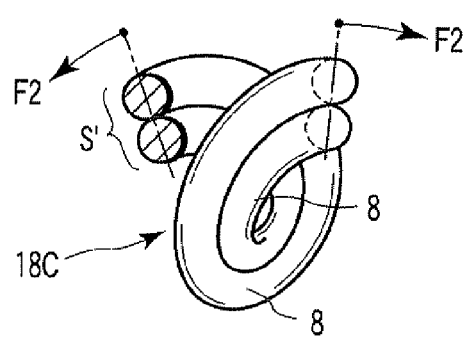
FIG. 25 is a conceptual view showing the twisted state of a wire when the close-wound coil of FIG. 23 is bent.

FIG. 23 to FIG. 25 show a fourth embodiment.

As shown in these drawings, a close-wound coil 20C of this embodiment is formed by winding a set of wires 18C formed by overlapping two circular-section wires 8 in the radial direction, spirally and closely over a predetermined length around a predetermined first axis O1. The set of wires 18C formed by overlapping two circular-section wires 8 in the radial direction (refer to FIG. 24) can make a section S' with a vertical-to-horizontal ratio larger than 1 similar to the section S of the wire 18 of the first embodiment. Therefore, the close-wound coil 20C formed by winding closely the set of wires 18C can also have the characteristics similar to the close-wound coil 20 of the first embodiment. Particularly, in this embodiment, only two wires 8 with the circular section are used, and it is unnecessary to roll the circular-section wire 8. Thus, it is easy to manufacture a coil with a large vertical-to-horizontal ratio.

Further, in this embodiment, as shown in FIG. 26 and FIG. 27, the wires 8 may be welded. In this case, as shown in FIG. 27, the two wires 8 are placed parallel and welded in their contacting parts, thereby forming a close-wound coil with a set of wires 18C combined and overlapped in the vertical direction. In this way, two wires 8 are made as one body, and the flexural rigidity of the set of wires 18C can be further increased.

FIG. 28 to FIG. 30 show a fifth embodiment of the present invention.

As show in these drawings, a close-wound coil 20D of this embodiment is formed by winding a wire 28 with a circular section (the vertical-to-horizontal ratio of the section is 1:1) spirally and closely over a predetermined length around a predetermined first axis O1. The wire 28 is not homogeneous in the inside, and the both side areas R1 and R1 (the areas with the crescent section) have low rigidity, and the area R2 (the area with a substantially rectangular section) near the center axis O2 held by these areas R1 and R1 has high rigidity.

Therefore, the wire 28 of this embodiment has the equivalent flexural rigidity and lower torsional rigidity, compared with a circular-section homogeneous material wire with the same dimension. Thus, the close-wound coil 20D of this embodiment is increased in the torsional rigidity and decreased in the flexural rigidity, compared with the close-wound coil formed by the homogeneous material wire, and the rotation transmission performance is increased.

As described above, according to this embodiment, it is possible to increase the rotation transmission performance while keeping the circular section shape of a wire. It is also possible to use the same manufacturing system as the circular-section wire. Further, since the vertical-to-horizontal dimension radio of a wire is 1:1, a fall-down during manufacturing is hard to occur, and the yield is increased.

Figure 31:
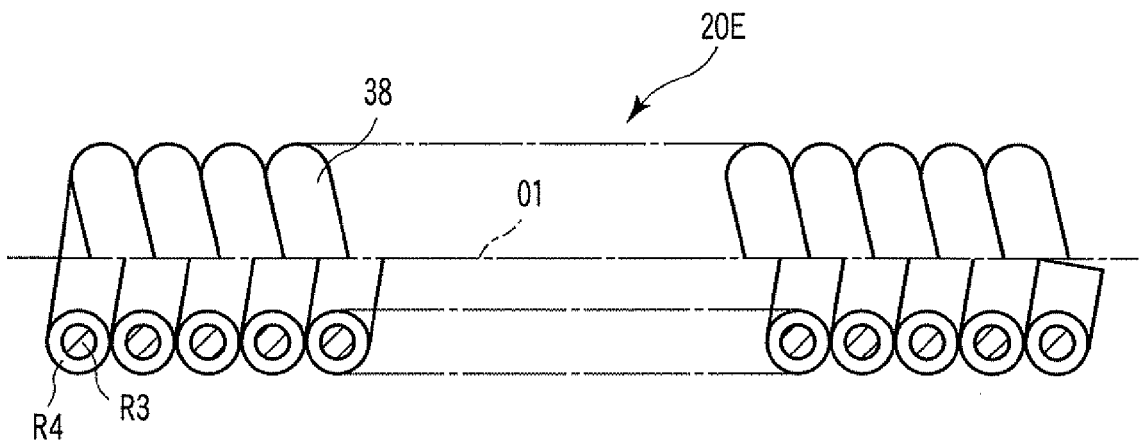
FIG. 31 is a half section view of a close-wound coil according to a sixth embodiment of the present invention.
Figure 32A:
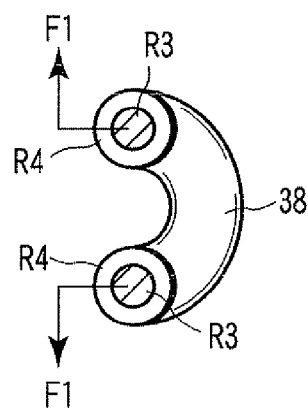
FIG. 32A is a conceptual view showing the bent state of a part of a wire forming a bending beam when the close-wound coil of FIG. 31 is twisted in the direction opposite to the winding direction.
Figure 32B:
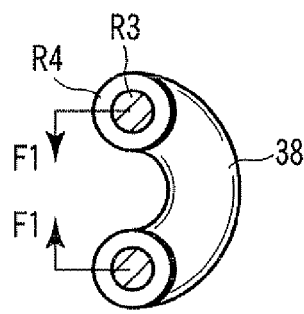
FIG. 32B is a conceptual view showing the bent state of a part of a wire forming a bending beam when the close-wound coil of FIG. 31 is twisted in the winding direction.
Figure 33:
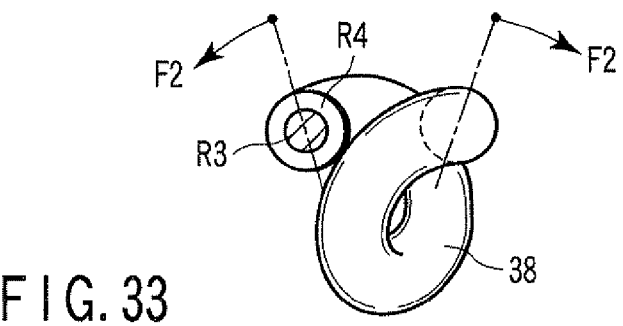
FIG. 33 is a conceptual view showing the twisted state of a wire when the close-wound coil of FIG. 31 is bent.

FIG. 31 to FIG. 33 show a sixth embodiment of the present invention.

As show in these drawings, a close-wound coil 20E of this embodiment is formed by winding a wire 38 with a circular section (the vertical-to-horizontal ratio of the section is 1:1) spirally and closely over a predetermined length around a predetermined first axis O1. The wire 38 is not homogeneous in the internal structure, and the central area R3 (the area with a circular section) has high rigidity, and the peripheral area R4 (the area with a ring-like section) has low rigidity.

Therefore, the wire 38 of this embodiment has the high flexural rigidity and lower torsional rigidity, compared with a circular homogeneous material wire of the same dimension. Thus, the close-wound coil 20E of this embodiment is increased in the torsional rigidity and decreased in the flexural rigidity, compared with the close-wound coil formed by the homogeneous material wire, and the rotation transmission performance is increased.

As described above, it is possible also in this embodiment to increase the rotation transmission performance while keeping the circular section shape of a wire. Therefore, the same functions and effects as the fifth embodiment can be obtained.

FIG. 34 to FIG. 36B show a seventh embodiment of the present invention.

As show in these drawings, a close-wound coil 20F of this embodiment is formed by winding a wire 48 with a circular section (the vertical-to-horizontal ratio of the section is 1:1) spirally and closely over a predetermined length around a predetermined first axis O1. The wire 48 uses the material with anisotropic flexural rigidity. This material has high flexural rigidity in a first direction, and low flexural rigidity in a second direction vertical to the first direction. In this embodiment, the first direction with high flexural rigidity is set orthogonal to the first axis O1 of the close-wound coil 20F.

Therefore, the wire 48 of this embodiment has the high flexural rigidity and lower torsional rigidity, compared with a circular homogeneous material wire of the same dimension. Thus, the close-wound coil 20F of this embodiment is increased in the torsional rigidity and decreased in the flexural rigidity, compared with the close-wound coil formed by the homogeneous material wire, and the rotation transmission performance is increased.

As described above, it is possible also in this embodiment to increase the rotation transmission performance while keeping the circular section shape of a wire. Therefore, the same functions and effects as the fifth embodiment can be obtained.

FIG. 37 to FIG. 40 show a first example of a medical treatment tool which uses one of the above-explained close-wound coils 20-20F as a force transmission member.

Figure 37:
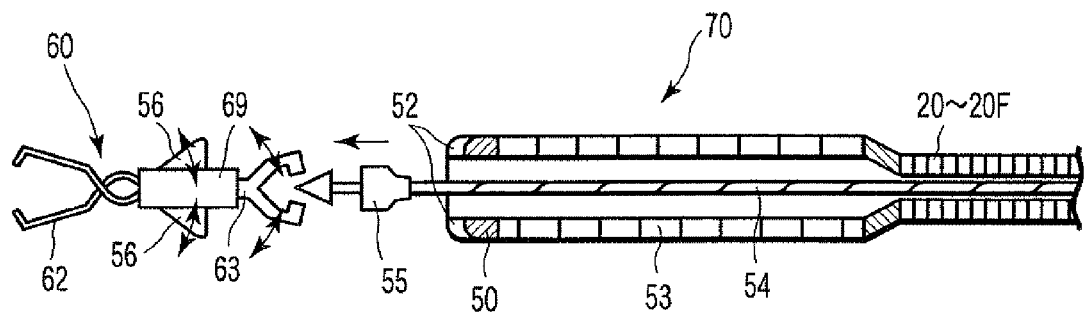
FIG. 37 is a partial side sectional view showing a first example of a medical treatment tool using the close-wound coil according to the first to seventh embodiment as a force transmission member.
Figure 38:
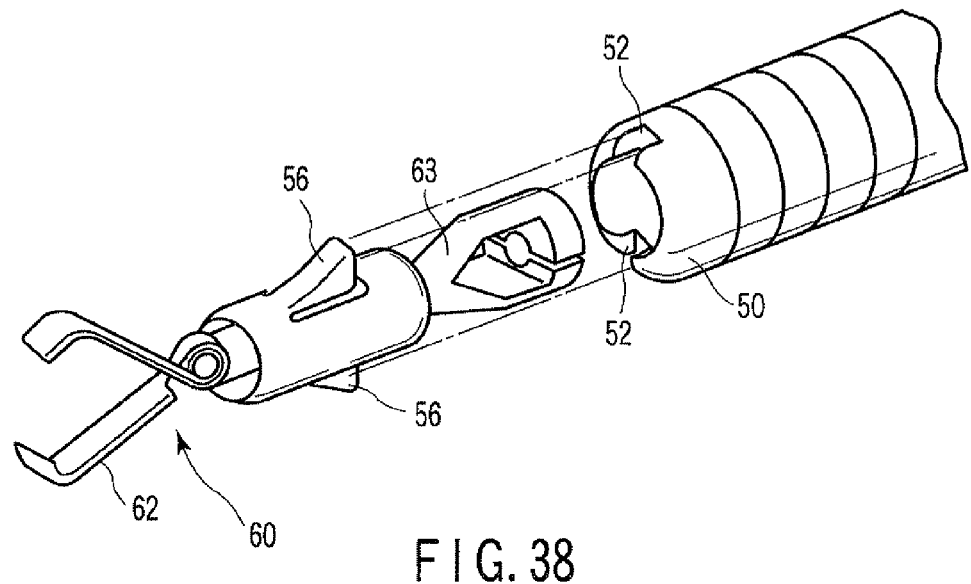
FIG. 38 is a perspective view of the distal end side of the treatment tool of FIG. 37.

As shown in FIG. 37 and FIG. 38, a medical treatment tool 70 of the first example has a clip 60 which can be left in the abdominal cavity as an end effector (treatment section). A distal end coil 53 with a large inside diameter is connected to the distal end side of the close-wound coil 20-20F. As the distal end coil 53 has the inside diameter larger than that of the close-wound coil 20-20F, the vertical-to-horizontal ratio of the section of the coil wire is lower than 1, and the rotation transmission performance is lower than that of the close-wound coil 20-20F.

Figure 40:
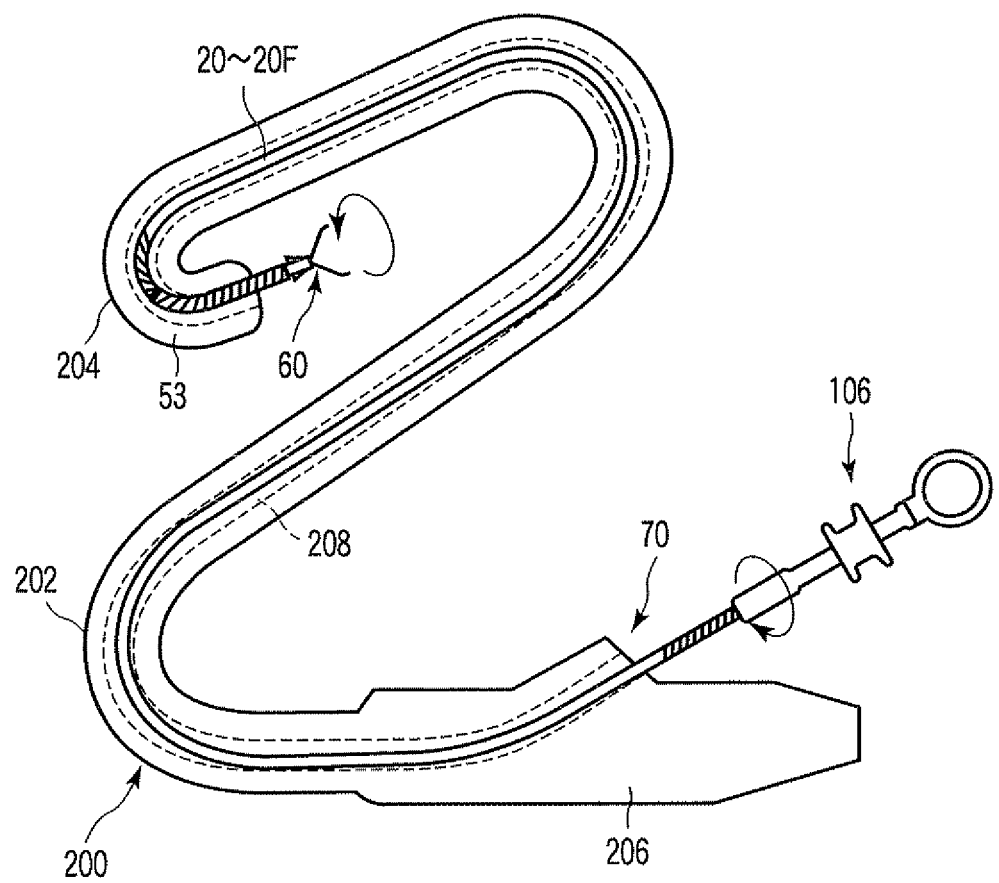
FIG. 40 is a schematic view showing the state that the treatment tool of FIG. 37 is inserted into an endoscope channel.

As shown in FIG. 40, the proximal end of the close-wound coil 20-20F is provided with a operation section (a rotation control section) 106 to rotate the close-wound coil 20-20F around the first axis O1.

A hook 55 which can be engaged with the clip 60 is provided at the distal end of a control wire 54 inserted into the close-wound coil 20-20F and the distal end coil 53. A chip 50 is fixed to the distal end of the close-wound coil 20-20F, and a notch 52 is formed vertically at the end of the chip 50.

The clip 60 is fixed to the hook 55 projected at the distal end. When the hook 55 is pushed into the rear end of the clip 60, the rear end of the clip 60 is deformed and the hook 55 is engaged with the clip 60 (refer to FIG. 39).

Figure 39A:
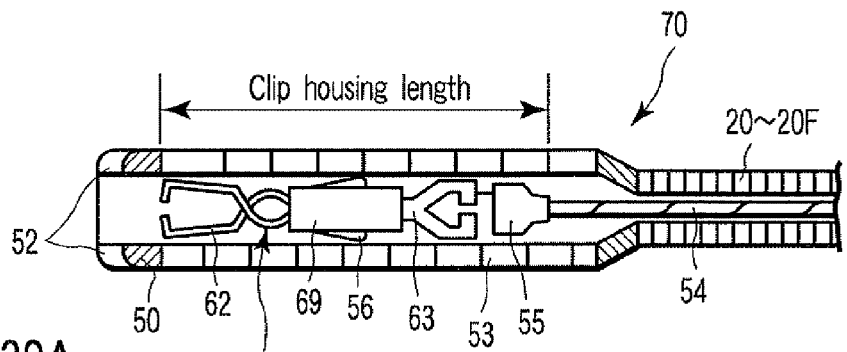
FIGS. 39A to 39D are partial side sectional views showing stepwise the action of the treatment tool of FIG. 37.

The clip 60 is provided with a retractable wing 56 (energized to the projected state), and the clip 60 can be retracted in the distal end coil 53 with the wing 56 folded (refer to FIG. 39A). The distal end coil 53 is set to the length capable of housing the clip 60.

As shown in FIG. 40, the medical treatment tool 70 is inserted into the channel 208 of the endoscope 200 with the clip 60 housed in the distal end coil 53 (the state shown in FIG. 39A), and led to a target part (e.g., a wound 80 shown in FIG. 39C) through the channel 208. In FIG. 40, the same reference numerals are given to the components common to those shown in FIG. 42.

Figure 39B:
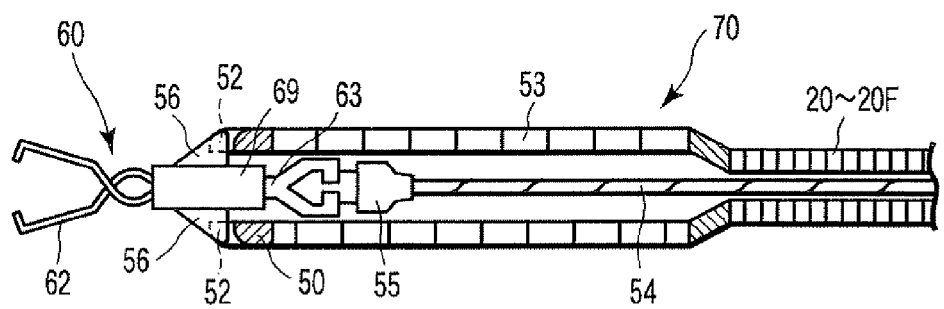
Figure 39C:
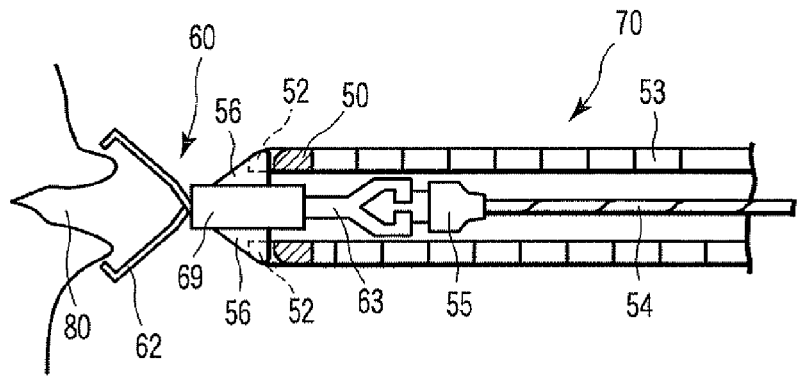
Figure 39D:
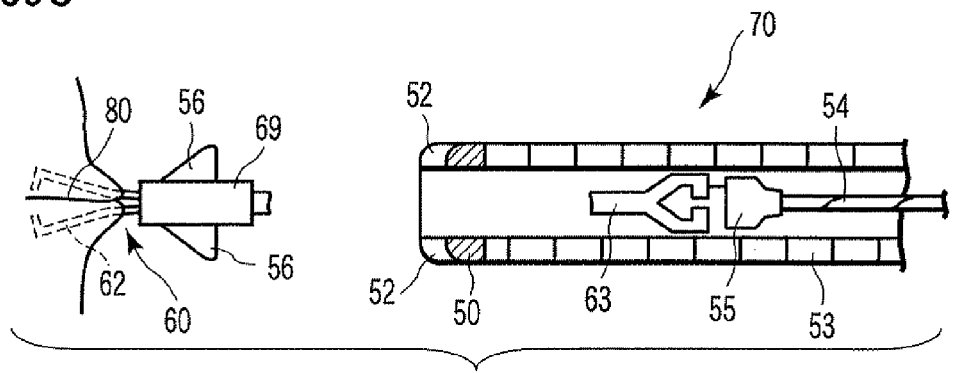

When the clip 60 is projected from the end of the distal end coil 53, the wing 56 projects to the outside, engages with the notch 52 of the distal end coil 53, receiving the pulling force acted on the clip 60 (refer to FIG. 39B). The hook 55 and clip 60 can rotate relatively, but as the wing 56 of the clip 60 is engaged with the notch 52 of the chip 50, the clip 60 is rotated following the rotation of the close-wound coil 20-20F.

When the pulling force is acted on the clip 60, a prong 62 is retracted into a holder tube 69, the arms of the prong 62 come close to each other, and the clip 60 can be completely closed. Therefore, the wound 80 can be closed by pressing the prong 62 to the wound 80 in a living body and pulling the clip 60. When the pulling force reaches a certain value, the material of a coupling 63 located between the clip 60 and hook 55 breaks, the clip 60 is divided into the front and rear parts, and the clip 60 can be left inside while closing the wound 80 (refer to FIG. 39C and FIG. 39D).

As explained above, since the flexural rigidity of the close-wound coil 20-20F is low, the medical treatment tool 70 can pass smoothly through the bending section 204 of the endoscope 200. Therefore, the length of the distal end coil 53 with low rotation transmission performance can be reduced as much as possible, and deterioration of the rotation transmission performance can be suppressed to the minimum.

Figure 41A:
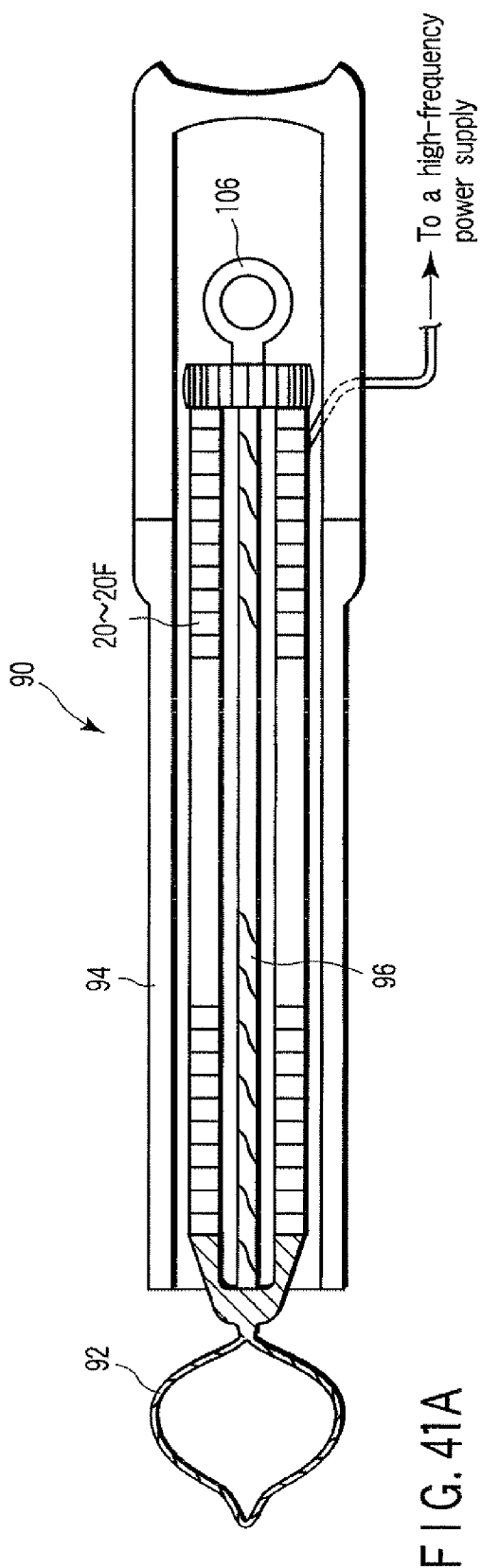
FIG. 41A is a partial side sectional view showing a second example of a medical treatment tool using the close-wound coil according to the first to seventh embodiment as a force transmission member.
Figure 41B:
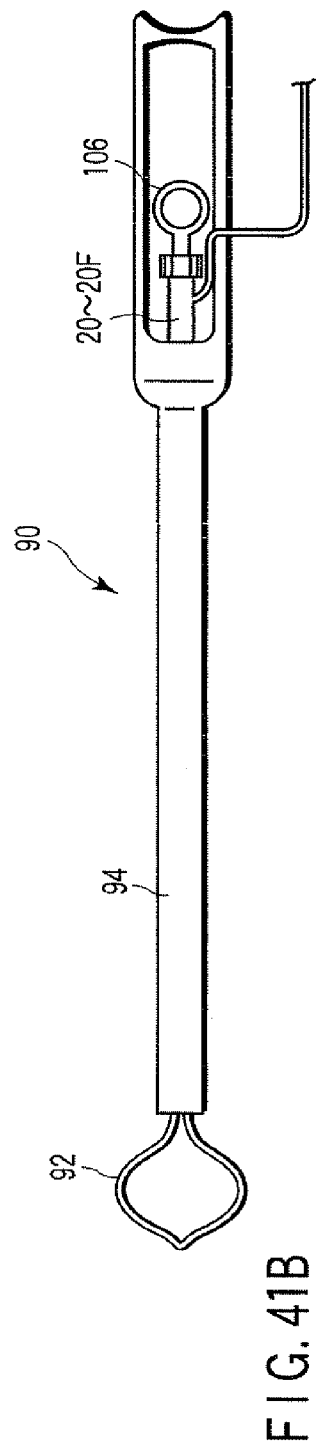
FIG. 41B is a plan view of the treatment tool of FIG. 41A.

FIG. 41A and FIG. 41B show a second example of a medical treatment tool which uses one of the above-explained close-wound coils 20-20F as a force transmission member.

As shown in the drawings, in a medical treatment tool 90 of the second example, a snare 92 is fixed to the distal end of the close-wound coil 20-20F as an end effector. A flexible mantle tube 94 is provided outside of the close-wound coil 20-20F. The mantle tube 94 and close-wound coil 20-20F are movable relatively in the axial direction, and also rotatable relatively. A reference numeral 96 denotes an extension control member which prevents extension of the close-wound coil 20-20F.

The snare 92 shrinks in the diameter when it is housed in the mantle tube 94, and is inserted into a body of a patient through the endoscope channel in being housed there. When the close-wound coil 20-20F is pushed out in the body and the snare 92 is projected from the mantle tube 94, the snare 92 is expanded. When the close-wound coil 20-20F is rotated in this state through the operation section 106 provided in the proximal end side of the close-wound coil 20-20F, the snare 92 is rotated together with the close-wound coil 20-20F with respect to the mantle tube 94, and positioned to an affected part, thereby the snare 92 can be placed around a pathological change such as a polyp. Pull the close-wound coil 20-20F with respect to the mantle tube 94 in this state. The snare 92 ties the polyp. Flow a high frequency current in the snare 92 through the close-wound coil 20-20F in this state. The snare cuts off the polyp.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical treatment tool comprising:
   a sheath-like member having a distal end, a proximal end and an inner bore extending along a longitudinal axis between the distal end and the proximal end;
   an end effector which is provided on the distal end of the sheath-like member;
   a control wire which is inserted into the sheath-like member for controlling the end effector, and connected to the end effector;
   a rotation control section which rotates the end effector following the rotation of the sheath-like member, the rotation control section comprising a first engagement section provided on the distal end of the sheath-like member and a second engagement section provided on the end effector, and controlling the rotation of the sheath-like member with respect to the end effector by the engagement of the first engagement section and the second engagement section; and
   a rotatable coupling which is provided between the end effector and the control wire, and which couples the control wire with the end effector in a relatively rotatable manner about a longitudinal axis of the control wire, wherein, when the end effector is rotated with a rotation of the sheath-like member through the rotation control section, the end effector is rotated relatively with respect to the control wire through the rotatable coupling.

2. A medical treatment tool comprising:
   a force transmission member having a distal end, a proximal end and an inner bore extending along a longitudinal axis between the distal end and the proximal end;
   a clip which is provided detachably with respect to the distal end of the force transmission member, the clip comprising arms having a distal end and a proximal end capable of gripping, and a holder tube provided on the proximal end side of the arms, the holder tube energizing the arms in a direction in which the distal ends come in contact with each other by drawing the proximal end of the arms inside;
   a control wire which is inserted into the force transmission member, and which is connected to the clip in a separable manner; and
   a rotation control section which rotates the clip following the rotation of the force transmission member, the rotation control section comprising a first engagement section provided on the distal end of the force transmission member and a second engagement section provided on the holder tube of the clip, and controlling the rotation of the force transmission member with respect to the clip by the engagement of the first engagement section and the second engagement section.

3. The medical treatment tool according to claim 2, wherein the first and second engagement sections are formed by contact areas which are provided respectively on the distal end of the force transmission member and the clip, and relative rotation is controlled when the contact areas are in contact with each other.

4. The medical treatment tool according to claim 2, wherein the second engagement section comprises a projection formed on the distal end of the holder tube, and the first engagement section comprises a notch formed on the force transmission member.

5. The medical treatment tool according to claim 2, further comprising a rotatable coupling which couples the control wire with the clip in a relatively rotatable manner about a longitudinal axis of the control wire, wherein, when the clip is rotated with a rotation of the force transmission member, the clip is rotated relatively with respect to the control wire by the rotatable coupling.

* * * * *